(12) United States Patent
Wong et al.

(10) Patent No.: US 8,010,196 B1
(45) Date of Patent: Aug. 30, 2011

(54) TISSUE CHARACTERIZATION USING INTRACARDIAC IMPEDANCES WITH AN IMPLANTABLE LEAD SYSTEM

(75) Inventors: Louis Wong, Sunnyvale, CA (US); Cem Shaquer, San Jose, CA (US); Gene A. Bornzin, Simi Valley, CA (US); Euljoon Park, Valencia, CA (US); Andre Walker, Monte Sereno, CA (US); Dorin Panescu, San Jose, CA (US); Jiong Xia, Stanford, CA (US); Shahrooz Shahparnia, Campbell, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 555 days.

(21) Appl. No.: 11/684,671

(22) Filed: Mar. 12, 2007

Related U.S. Application Data

(60) Provisional application No. 60/787,884, filed on Mar. 31, 2006.

(51) Int. Cl.
*A61N 1/18* (2006.01)

(52) U.S. Cl. .................... 607/28; 607/2; 607/9; 607/17; 600/547

(58) Field of Classification Search ............... 600/442, 600/547; 607/2, 8, 26, 28, 45, 66, 68, 69, 607/76

See application file for complete search history.

(56) References Cited

U.S. PATENT DOCUMENTS

| | | | |
|---|---|---|---|
| 3,934,458 A | 1/1976 | Beretsky | |
| 4,512,195 A * | 4/1985 | Miwa et al. ................ | 73/602 |
| 4,535,774 A | 8/1985 | Olson | |
| 4,686,987 A | 8/1987 | Salo et al. | |
| 5,003,976 A | 4/1991 | Alt | |
| 5,042,303 A | 8/1991 | Geluk | |
| 5,179,946 A | 1/1993 | Weiss | |
| 5,190,035 A | 3/1993 | Salo et al. | |
| 5,201,865 A | 4/1993 | Kuehn | |
| 5,282,840 A | 2/1994 | Hudrlik | |

(Continued)

FOREIGN PATENT DOCUMENTS

WO 9615827 A1 5/1996

(Continued)

OTHER PUBLICATIONS

Non-Final Office Action mailed Jun. 10, 2009: Related U.S. Appl. No. 11/684,677.

(Continued)

*Primary Examiner* — Carl H Layno
*Assistant Examiner* — Pamela M Bays
(74) *Attorney, Agent, or Firm* — Theresa Takeuchi; Steven M. Mitchell

(57) ABSTRACT

An implantable system acquires intracardiac impedance with an implantable lead system. In one implementation, the system generates frequency-rich, low energy, multi-phasic waveforms that provide a net-zero charge and a net-zero voltage. When applied to bodily tissues, current pulses or voltage pulses having the multi-phasic waveform provide increased specificity and sensitivity in probing tissue. The effects of the applied pulses are sensed as a corresponding waveform. The waveforms of the applied and sensed pulses can be integrated to obtain corresponding area values that represent the current and voltage across a spectrum of frequencies. These areas can be compared to obtain a reliable impedance value for the tissue. Frequency response, phase delay, and response to modulated pulse width can also be measured to determine a relative capacitance of the tissue, indicative of infarcted tissue, blood to tissue ratio, degree of edema, and other physiological parameters.

22 Claims, 28 Drawing Sheets

U.S. PATENT DOCUMENTS

| | | | |
|---|---|---|---|
| 5,300,093 | A | 4/1994 | Koestner et al. |
| 5,324,309 | A | 6/1994 | Kallok |
| 5,344,429 | A | 9/1994 | Smits |
| 5,507,785 | A | 4/1996 | Deno |
| 5,531,772 | A | 7/1996 | Prutchi |
| 5,601,608 | A | 2/1997 | Mouchawar |
| 5,713,935 | A | 2/1998 | Prutchi et al. |
| 5,746,214 | A * | 5/1998 | Brown et al. .......... 600/547 |
| 5,800,467 | A | 9/1998 | Park |
| 5,814,088 | A | 9/1998 | Paul |
| 5,957,861 | A | 9/1999 | Combs et al. |
| 6,002,966 | A | 12/1999 | Loeb |
| 6,044,294 | A | 3/2000 | Mortazavi |
| 6,198,965 | B1 | 3/2001 | Penner |
| 6,219,579 | B1 | 4/2001 | Bakels |
| 6,223,082 | B1 | 4/2001 | Bakels |
| 6,251,303 | B1 | 6/2001 | Bawendi |
| 6,253,103 | B1 | 6/2001 | Baura |
| 6,269,264 | B1 | 7/2001 | Weyant |
| 6,275,727 | B1 | 8/2001 | Hopper |
| 6,278,894 | B1 | 8/2001 | Salo et al. |
| 6,337,994 | B1 | 1/2002 | Stoianovici |
| 6,339,722 | B1 | 1/2002 | Heethaar |
| 6,459,929 | B1 | 10/2002 | Hopper |
| 6,473,640 | B1 | 10/2002 | Eriebacher |
| 6,473,647 | B1 | 10/2002 | Bradley |
| 6,501,983 | B1 | 12/2002 | Natarajan |
| 6,512,942 | B1 | 1/2003 | Burdette |
| 6,512,949 | B1 | 1/2003 | Combs |
| 6,527,729 | B1 | 3/2003 | Turcott |
| 6,539,261 | B2 | 3/2003 | Dal Molin |
| 6,595,927 | B2 | 7/2003 | Pitts-Crick |
| 6,620,186 | B2 | 9/2003 | Saphon |
| 6,754,530 | B2 | 6/2004 | Bakels |
| 6,970,742 | B2 | 11/2005 | Mann |
| 7,010,347 | B2 | 3/2006 | Schecter |
| 7,065,400 | B2 | 6/2006 | Schechter |
| 7,065,403 | B1 | 6/2006 | Mouchawar |
| 7,139,610 | B2 | 11/2006 | Ferek-Petric |
| 7,184,821 | B2 | 2/2007 | Belalcazar |
| 7,200,442 | B1 | 4/2007 | Koh |
| 7,251,524 | B1 | 7/2007 | Hepp |
| 7,272,443 | B2 | 9/2007 | Min |
| 7,410,467 | B2 | 8/2008 | Cooper |
| 7,488,290 | B1 | 2/2009 | Stahmann |
| 2001/0051774 | A1 | 12/2001 | Littrup |
| 2002/0002389 | A1 | 1/2002 | Bradley |
| 2003/0083712 | A1 | 5/2003 | Rueter |
| 2003/0216630 | A1 | 11/2003 | Jersey-Willuhn |
| 2003/0220556 | A1* | 11/2003 | Porat et al. .......... 600/407 |
| 2004/0015196 | A1 | 1/2004 | Holmstrom |
| 2004/0059220 | A1 | 3/2004 | Mourad |
| 2004/0064161 | A1 | 4/2004 | Gunderson |
| 2004/0215097 | A1 | 10/2004 | Wang |
| 2004/0220640 | A1 | 11/2004 | Burnes |
| 2004/0230112 | A1* | 11/2004 | Scholz .......... 600/407 |
| 2005/0021103 | A1 | 1/2005 | DiLorenzo |
| 2005/0124908 | A1 | 6/2005 | Belalcazar |
| 2005/0215914 | A1 | 9/2005 | Bornzin |
| 2005/0216067 | A1 | 9/2005 | Min |
| 2005/0283091 | A1* | 12/2005 | Kink et al. .......... 600/547 |
| 2006/0025828 | A1 | 2/2006 | Armstrong |
| 2006/0100539 | A1 | 5/2006 | Min |
| 2006/0129196 | A1 | 6/2006 | Dong |
| 2006/0135886 | A1* | 6/2006 | Lippert et al. .......... 600/547 |
| 2006/0184060 | A1 | 8/2006 | Belalcazar |
| 2006/0235480 | A1 | 10/2006 | Schecter |
| 2006/0241512 | A1 | 10/2006 | Kwok |
| 2006/0293609 | A1 | 12/2006 | Stahmann |
| 2008/0009759 | A1 | 1/2008 | Chetham |
| 2008/0033498 | A1 | 2/2008 | Mann |
| 2008/0221477 | A1 | 9/2008 | Olson |
| 2009/0018597 | A1 | 1/2009 | Wenzel |
| 2009/0287267 | A1 | 11/2009 | Wenzel |

FOREIGN PATENT DOCUMENTS

| | | |
|---|---|---|
| WO | WO 96/15827 | 5/1996 |
| WO | 9619260 A1 | 6/1996 |
| WO | WO 96/19260 | 6/1996 |
| WO | 9807467 A1 | 2/1998 |
| WO | WO 98/07467 | 2/1998 |
| WO | WO 0113792 A1 | 3/2001 |
| WO | WO 0132260 A1 | 5/2001 |
| WO | 0187410 A2 | 11/2001 |
| WO | 0187410 A3 | 11/2001 |
| WO | WO 01/87410 A2 | 11/2001 |
| WO | WO 01/87410 A3 | 11/2001 |
| WO | WO 2004096041 A2 | 11/2004 |
| WO | WO 2004096041 A3 | 11/2004 |
| WO | WO 2004105862 | 12/2004 |

OTHER PUBLICATIONS

Non-Final Office Action mailed May 27, 2009: Related U.S. Appl. No. 11/684,681.
Non-Final Office Action mailed Apr. 6, 2009: Related U.S. Appl. No. 11/558,101.
Non-Final Office Action mailed Feb. 3, 2009; Related U.S. Appl. No. 11/557,851.
Non-Final Office Action mailed May 29, 2009: Related U.S. Appl. No. 11/557,870.
Non-Final Office Action mailed Jun. 10, 2009: Related U.S. Appl. No. 11/557,882.
Non-Final Office Action mailed Jun. 19, 2009 Related U.S. Appl. No. 11/684,664.
Non-Final Office Action mailed Jun. 23, 2009 Related U.S. Appl. No. 11/558,088.
Final Office Action mailed Jan. 25, 2010: Related U.S. Appl. No. 11/684,664.
Advisory Action mailed Apr. 12, 2010: Related U.S. Appl. No. 11/684,664.
Final Office Action mailed Jan. 21, 2010: Related U.S. Appl. No. 11/684,677.
Advisory Action mailed Apr. 14, 2010: Related U.S. Appl. No. 11/684,677.
Final Office Action mailed Feb. 3, 2010: Related U.S. Appl. No. 11/684,681.
Advisory Action mailed Apr. 14, 2010: Related U.S. Appl. No. 11/684,681.
Non-Final Office Action mailed Aug. 20, 2009: Related U.S. Appl. No. 11/684,688.
Final Office Action mailed Jan. 21, 2010: Related U.S. Appl. No. 11/684,688.
Advisory Action mailed Apr. 12, 2010: Related U.S. Appl. No. 11/684,688.
Final Office Action mailed Oct. 8, 2009: Related U.S. Appl. No. 11/558,101.
Advisory Action mailed Feb. 4, 2010: Related U.S. Appl. No. 11/558,101.
Final Office Action mailed Nov. 13, 2009: Related U.S. Appl. No. 11/557,851.
Advisory Action mailed Feb. 22, 2010: Related U.S. Appl. No. 11/557,851.
Final Office Action mailed Mar. 3, 2010: Related U.S. Appl. No. 11/557,870.
Final Office Action mailed Mar. 26, 2010: Related U.S. Appl. No. 11/557,882.
Final Office Action mailed Jan. 29, 2010: Related U.S. Appl. No. 11/558,088.
Non-Final Office Action mailed Sep. 15, 2009: Related U.S Appl. No. 11/559,235.
Final Office Action mailed Jan. 29, 2010: Related U.S. Appl. No. 11/559,235.
Notice of Allowance mailed Apr. 2, 2010: Related U.S. Appl. No. 11/559,235.
Stutz, "All About Circuits: Conductance." Copyright 1999-2000. <http://www.allaboutcircuits.com/vol_1/chpt_5/4.html>.
Non-Final Office Action mailed Oct. 5, 2010: Related U.S. Appl. No. 11/684,677.

Notice of Allwance mailed Jan. 25, 2011: Related U.S. Appl. No. 11/684,677.
Notice of Allowance mailed Oct. 4, 2010: Related U.S. Appl. No. 11/684,681.
Notice of Allowance mailed Jan. 31, 2011: Related U.S. Appl. No. 11/684,681.
Non-Final Office Action mailed Mar. 25, 2011: Related U.S. Appl. No. 11/684,688.
Final Office Action mailed May 27, 2010: Related U.S. Appl. No. 11/557,870.
Advisory Action mailed Aug. 5, 2010: Related U.S. Appl. No. 11/557,870.
Final Office Action mailed Apr. 30, 2010: Related U.S. Appl. No. 11/557,882.
Advisory Action mailed Aug. 2, 2010: Related U.S. Appl. No. 11/557,882.
Non-Final Office Action mailed May 11, 2010: Related U.S. Appl. No. 11/558,088.
Final Office Action mailed Nov. 12, 2010: Related U.S. Appl. No. 11/558,088.
Notice of Allowance mailed Jul. 19, 2010: Related U.S. Appl. No. 11/559,235.
Min et al., "Modification of Pulse Wave Signals in Electrical Bioimpedance Analyzers for Implantable Medical Devices" Proceedings of the 26th Annual International Conference of the IEEE EMBS; San Franciso, CA; Sep. 1-5, 2004.

* cited by examiner

Different Impedance Measurement Configurations

IMPEDANCE MEASUREMENT CIRCUIT ARCHITECTURE
(INJECTED CURRENT – SENSED VOLTAGE VERSION)

PREAMPLIFIER TIMING DIAGRAM

Auto-zero Phase:
1. Block All DC Component
2. Cancel All Half-cell Electrode's Potentials, Which Can Be -0.5volts
3. Auto-adjust Op-amp Offsets

PREAMPLIFIER BLOCK DIAGRAM

SIGN-CONVERTING, DIFFERENTIAL-TO-SINGLE-ENDED INTEGRATOR

TIMING DIAGRAM

TIMING DIAGRAM

DISCRETE TO CONTINUOUS SIGNAL CONVERTER

ASYMMETRICAL TRI-PHASIC PULSE WAVEFORM

FREQUENCY COMPONENTS OF ASYMMETRIC TRI-PHASIC PULSE WAVEFORM

SCOPE SHOT OF AN ASYMMETRICAL VOLTAGE PULSE WAVEFORM

Symmetrical Tri-phasic Pulse Waveform

Frequency Components of Symmetric Tri-phasic Pulse Waveform

Scope Shot of a Symmetrical Voltage Pulse Waveform

Sinc[x] Function

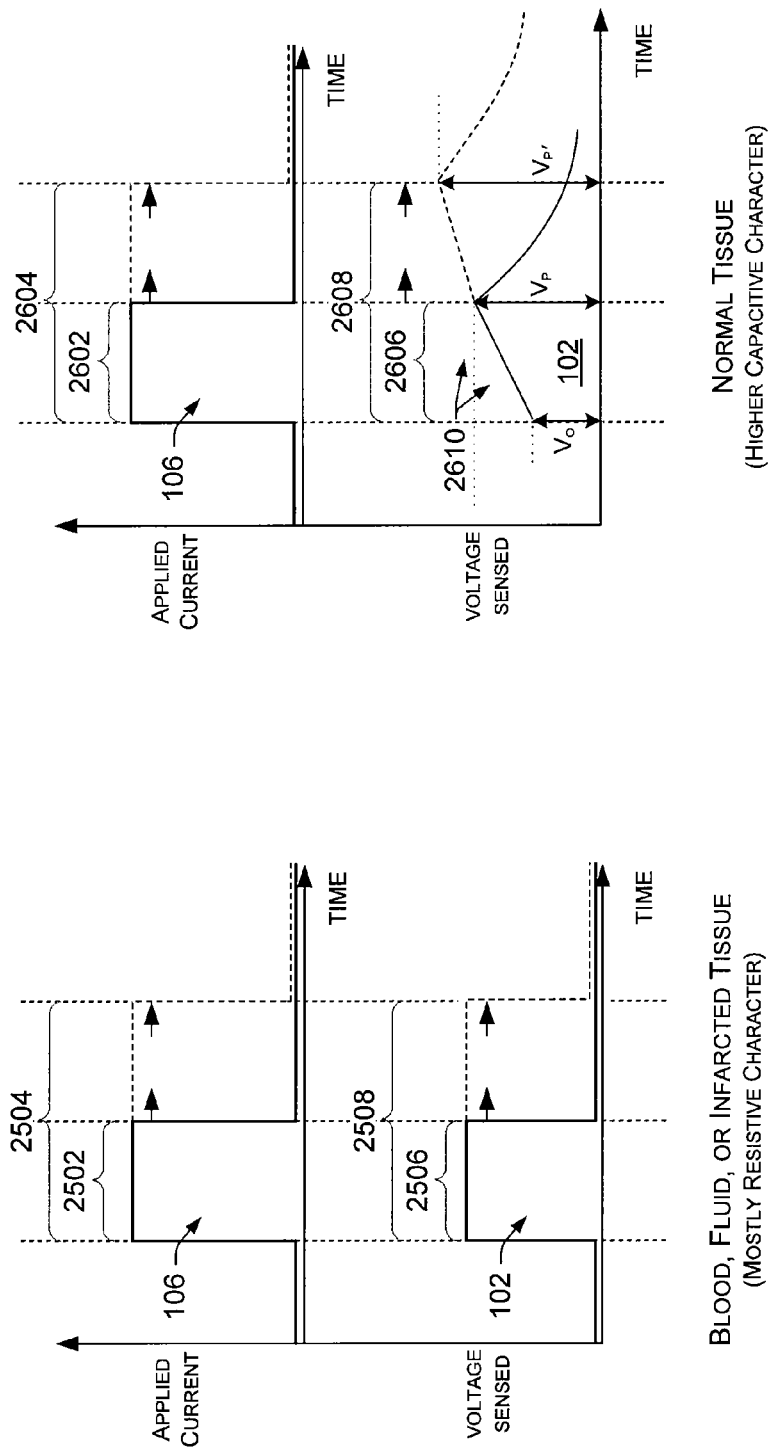

TISSUE CHARACTERIZATION USING INTRACARDIAC IMPEDANCES WITH AN IMPLANTABLE LEAD SYSTEM

PRIORITY CLAIM AND RELATED APPLICATIONS

This application claims priority under 35 U.S.C. 119(e) to U.S. Provisional Patent Application No. 60/787,884 filed Mar. 31, 2006, which is incorporated herein by reference. This application is related to U.S. patent application Ser. Nos. 11/684,664, 11/684,667, 11/684,681, and 11/684,688, each entitled "Tissue Characterization Using Intracardiac Impedances with an Implantable Lead System," filed concurrently on Jan. 18, 2007. Each of the foregoing applications is fully incorporated by reference herein.

TECHNICAL FIELD

Subject matter presented herein relates generally to implantable medical devices and more particularly to acquiring intracardiac impedances with an implantable lead system.

BACKGROUND

Implantable medical devices often try to measure as many physiological parameters as possible with components already available in the implantable device or with minimal changes to the existing hardware. This is especially true when a device, such as an implantable cardioverter-defibrillator (ICD), contains an impressive array of electronic hardware and programmable software components. These components can be leveraged to shed light on many patient medical conditions without extra design cost. Thus, these components are sometimes used for measuring physiological variables not directly related to the primary cardiac functionality of an ICD, such as measuring changes in thoracic impedance in order to track respiration.

Because ability to measure some of these physiological parameters has been added to implantable devices as an afterthought, it can happen that such measurements are not performed in the best manner, since an implantable device retrofitted to perform ancillary measurements is intended primarily for a different purpose.

Some conventional devices try to analogize impedance results in the body from simple resistance measurements between two points in the body. These results are suspect because there are few electrical pathways in the body with impedances that can be reliably described by simple resistance measurements. These resistance measurements sometimes try to measure hemodynamic variables, cardiac parameters, presence of edema, tissue changes, etc. Measurement of these parameters places a heavy burden on crude resistance measurements, especially if the electrical pulses used to perform the resistance measurements change the parameter being measured or if the conventional implanted device does not properly filter out extraneous influences that interfere with such measurements. Thus, some conventional techniques used by implanted devices for deriving impedance values in the body are half-hearted or unsophisticated attempts at making what should be a more thorough measurement, and thus result in inaccuracy and low reliability.

The assumption that a resistance measurement is truly describing a bodily impedance can result in some false negatives. For example, a pathological condition being tracked may really be present, but the conventional implanted device does not detect it due to a lack of sensitivity of the measurements or because the conventional technique examines only a limited pathway of tissue.

Conventional reliance on a resistance component of impedance may also lead an implanted device to false positives, in which measurements indicate presence of the pathological condition, but the conventional technique is actually measuring something else entirely. For example, a conventional device may send out a sensing signal that causes a change in an ionic balance, which the conventional device then erroneously interprets as a change in the physiological parameter being measured.

Trying to sample a signal at points in time that are contrived to coincide synchronously with applied pulses is a very unreliable conventional pitfall. This conventional approach is nearly impossible to successfully implement, because the effects of phase delay, cardiac cycle, respiratory cycle, etc., would have to be known beforehand to successfully synchronize "snapshot" sampling measurements with the timing of applied pulses. These influencing effects that need to be known beforehand are actually components of the parameter being measured, thus the synchronization is typically faulty and the obtained measurements are inaccurate.

SUMMARY

An implantable system acquires intracardiac impedance with an implantable lead system. In one implementation, the system generates frequency-rich, low energy, multi-phasic waveforms that provide a net-zero charge and a net-zero voltage. When applied to bodily tissues, current pulses or voltage pulses having the multi-phasic waveform provide increased specificity and sensitivity in probing tissue. The effects of the applied pulses are sensed as a corresponding waveform. The waveforms of the applied and sensed pulses can be integrated to obtain corresponding area values that represent the current and voltage across a spectrum of frequencies. These areas can be compared to obtain a reliable impedance value for the tissue. Frequency response, phase delay, and response to modulated pulse width can also be measured to determine a relative capacitance of the tissue, indicative of infarcted tissue, blood to tissue ratio, degree of edema, and other physiological parameters.

BRIEF DESCRIPTION OF THE DRAWINGS

FIG. 25 is a diagram of an exemplary waveform shape response of infarcted tissue to modulated width of applied current pulse waveforms.

FIG. 26 is a diagram of an exemplary waveform shape response of normal tissue to modulated width of applied current pulse waveforms.

DETAILED DESCRIPTION

This disclosure describes exemplary implantable devices that create special electrical waveforms for probing tissues and measuring physiological conditions inside the human body. In one implementation, an implantable device injects an exemplary electrical waveform inside the body and senses the results. As used herein, "inject" will be used to mean sending an electrical signal from a circuit of the implantable device into human tissue.

Figure 1:
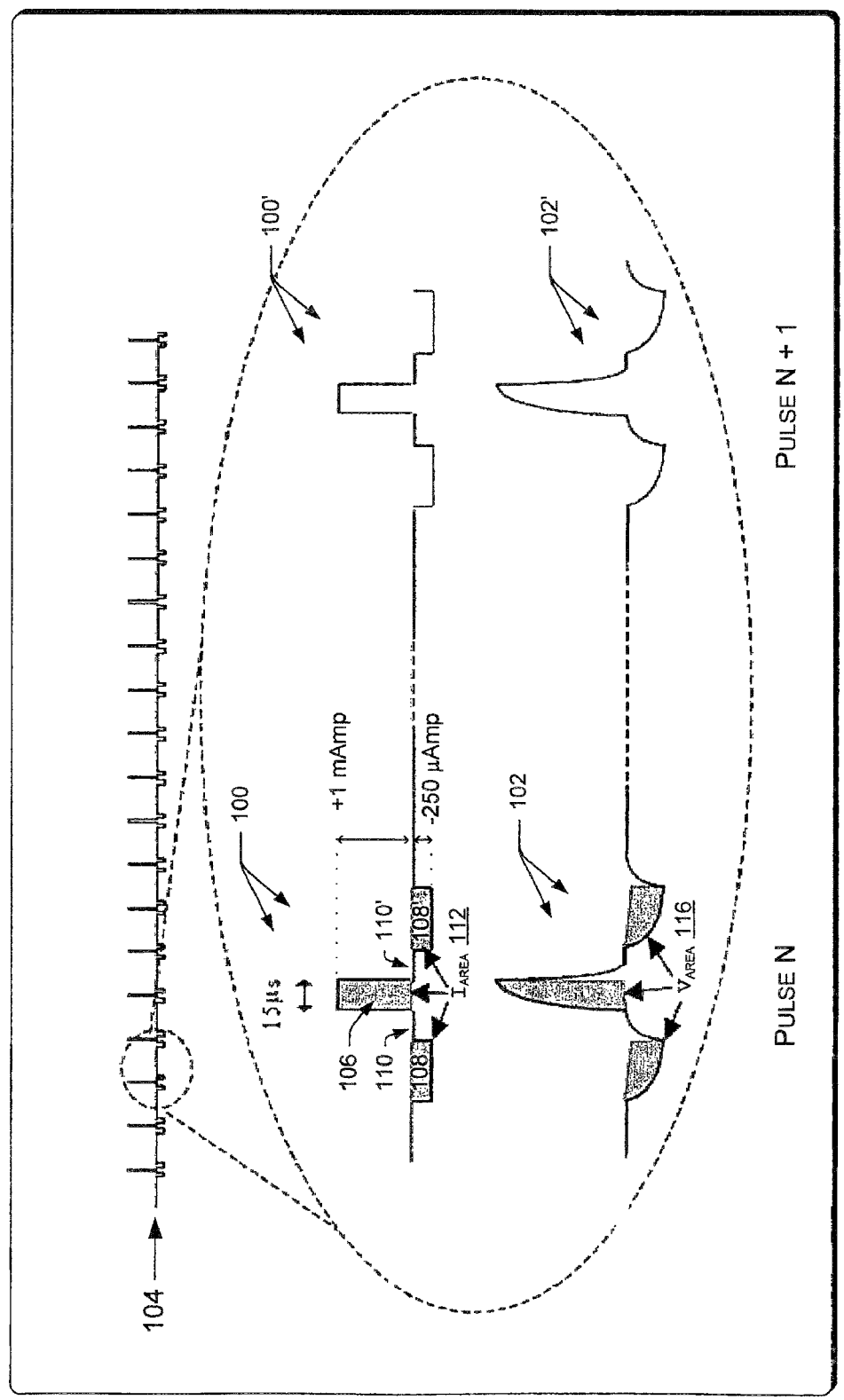
FIG. 1 is a diagram of exemplary pulse waveforms.

As shown in FIG. 1, an exemplary pulse waveform 100 possesses many special waveform features and electrical characteristics that are well suited for measuring many types of physiological parameters in the body using current modulated or voltage modulated pulses. Exemplary pulse waveforms 100 (hereinafter, "waveforms") are multi-phasic, with negative phases (pulse segments below baseline) that balance positive phases (pulse segments above baseline). The illustrated waveform is tri-phasic. Each exemplary waveform 100 can be either a current pulse waveform or a voltage pulse waveform. For example, in one implementation a current pulse waveform 100 is injected and results are sensed as a voltage waveform 102 that may roughly correspond to the injected waveform 100.

When used in a wave train 104, the special features of the waveform 100 provide an implantable device with opportunities to perform many kinds of measurements and tests without extensive modification of the implantable device. That is, once generated, exemplary waveforms, such as waveform 100, "self-include" many wave features that can be probative of physiological conditions without requiring the implantable device to carry awkward amounts of circuitry or exotic components. Rather, an implantable device can reasonably leverage an exemplary waveform 100 to efficiently collect many kinds of physiological data. This is better than relying on extensive hardware enhancements in the implantable device to try to manipulate a conventional signal in order to attempt collection of extra data. For example, since the exemplary waveforms 100 themselves carry wide frequency spectrum content, there is no need to provide special injection circuitry to perform a frequency sweep using a conventionally injected signal.

The design of these exemplary waveforms, e.g., waveform 100, has been optimized across various principles of physics and electrochemistry to exploit the science of electrical measurement inside the human body and to provide greater efficiency and patient comfort. Thus, the design of the waveform 100 aims to maximize the amount of data gathered while minimizing the amount of energy used to do so.

Exemplary properties of the exemplary waveforms 100 described herein include better penetration of some tissues than conventionally injected signals; better differential penetration of tissues than conventionally injected signals for improved differentiation and characterization of tissues; fuller frequency spectrum content than conventionally injected signals in order to return richer detail in the sensed results; greater neutrality in the body than conventionally injected signals, i.e., exemplary waveforms aim to "do no harm" and do not change the parameter they are trying to measure, and moreover, do not create ionic imbalances or imbalances of charge, voltage, etc., in the tissues or at tissue-electrode interfaces.

The exemplary waveforms 100 have a far shorter wavelength (e.g., 100 microseconds from beginning to end of a pulse) than some conventionally injected signals (e.g., 30 milliseconds for conventional) and are not only charge balanced but also voltage balanced to have a net-zero voltage and a net-zero charge. It is important to note that the net-zero voltage feature, also referred to as the voltage-balanced feature, refers to the voltage formed on blocking capacitors that appear in series with the load. The flow of current through these capacitors builds up voltage across them. Since these capacitors, such as capacitor 628 in FIG. 6, also appear in circuits that are responsible for sensing cardiac activity, it is important that the net voltage built up on them be zero. As a result of the net-zero voltage feature, the influence of an exemplary waveform 100 on sensing cardiac activity will be minimal. Thus, a current with a waveform such as that presented in FIGS. 16 and 19, generates a voltage across capacitor 628 that has a zero-volt mean value. In some implementations, the shorter wavelength features (e.g., 15 microseconds for the positive phase 106) can allow detection and location of smaller features than a larger wavelength signal could. Because of the short wavelength features and phase balancing between positive phase(s) 106 and negative phases 108, polarizations and other disturbances of tissue and equipment are minimized along measurement pathways—the pulses have come and gone before the environment can "wake up" to their presence. Because an exemplary waveform 100 has variegated waveform features, such as different positive phase and negative phase wave shapes, numerous frequencies are available for sensing physiological conditions when the waveform 100 is injected.

Another feature of exemplary waveforms 100 is inclusion of null segments 110—intra-waveform segments containing no signal—that serve the purpose of allowing the electronics in the processing circuit to settle.

In one implementation, the exemplary waveform 100 is used to derive physiological measurements based on intracardiac impedances. Based on such cardiogenic impedance measurements, many physiological variables can be trended to detect changes in a patient's condition, such as congestive heart failure (CHF) index, pulmonary edema, systolic slope, contraction (e.g., dZ/dt(max)), diastolic slope, relaxation (e.g., dZ/dt(min)), pre-ejection period (in low resolution), ejection time, left ventricular ejection fraction (LVEF), diastolic heart failure index (DHFI), cardiac index, etc.

The exemplary waveform 100 provides an elegant and reliable vehicle for measuring bodily impedances in a manner that gives reliably reproducible results. Instead of a conventional technique of trying to sense an instantaneous "snapshot" measurement of a conventionally injected signal, an exemplary method derives an impedance measurement by dividing the area under the sensed voltage curve (waveform 102) by the area of the injected current waveform 100. An exemplary implantable device can perform this exemplary method by "integrating the curve" of an absolute value of waveforms 100 or 102. Sometimes the exemplary implantable device can closely approximate this integration without having to perform an integration operation by directly measuring and summing the area 112 "under" the curve (e.g., under the rectangular wave) of the waveform 100, that is, the area 112 composed of the absolute value of the three areas of the three phases of an exemplary tri-phasic waveform 100.

Likewise, the exemplary implantable device can integrate, or closely approximate the integration, by measuring and summing the area 116 "under" the curve (e.g., the square wave) of the waveform 102, that is, the area 116 composed of the absolute value of the three areas of the three phases.

In one implementation, the area of the sensed voltage, 116, is measured at the output of an integrator circuit. The area of the injected current, 112, is computed by, or preset by, the micro-controller driving the implantable device.

An implantable device may thus use this area-based ("areal") approach to deriving a network of impedance measurements over one-vector or over a multi-vector network. One reason that this exemplary method is elegant and stable is that the area 116 of the sensed waveform 102 represents the body's response to the injected waveform 100 across all the frequencies contained in the injected waveform 100. That is, the area 116 of the sensed waveform 102 represents all the frequency harmonics of the injected waveform 100. This is very valuable when frequency response is used as the probing tool provided by the exemplary waveform 100. It should be noted that the injected waveform 100 does not supply a net direct current (DC)—there is no DC component to measure in the sensed waveform 102.

Measuring area under waveforms instead of taking instantaneous measurements of an electrical quantity solves the conventional problem that occurs when merely sampling signals, i.e., the problem of erroneously assuming that the injected signal and the sensed signal will be in phase. This perfect phase alignment rarely occurs in living systems because of the capacitive content of living tissue. Thus, when signal sampling, if there is a delay in voltage coming back to measurement circuitry (e.g., if voltage lags current) an incorrect value will be sensed because internal capacitors and other sampling circuitry do not have enough time to settle to handle that delay. If the injection path has some capacitive character, then the area of the sensed voltage waveform 102 is shifted to the right (temporally delayed), depending on the degree of capacitive character. Measuring total combined area can occur after the entire integration process terminates—and this is less prone to inaccuracy from time shifts between injected waveform and sensed results. In some implementations to be described below, this allowed phase delay is actually exploited to return even more physiological information.

Exemplary Implantable Device

Figure 2:
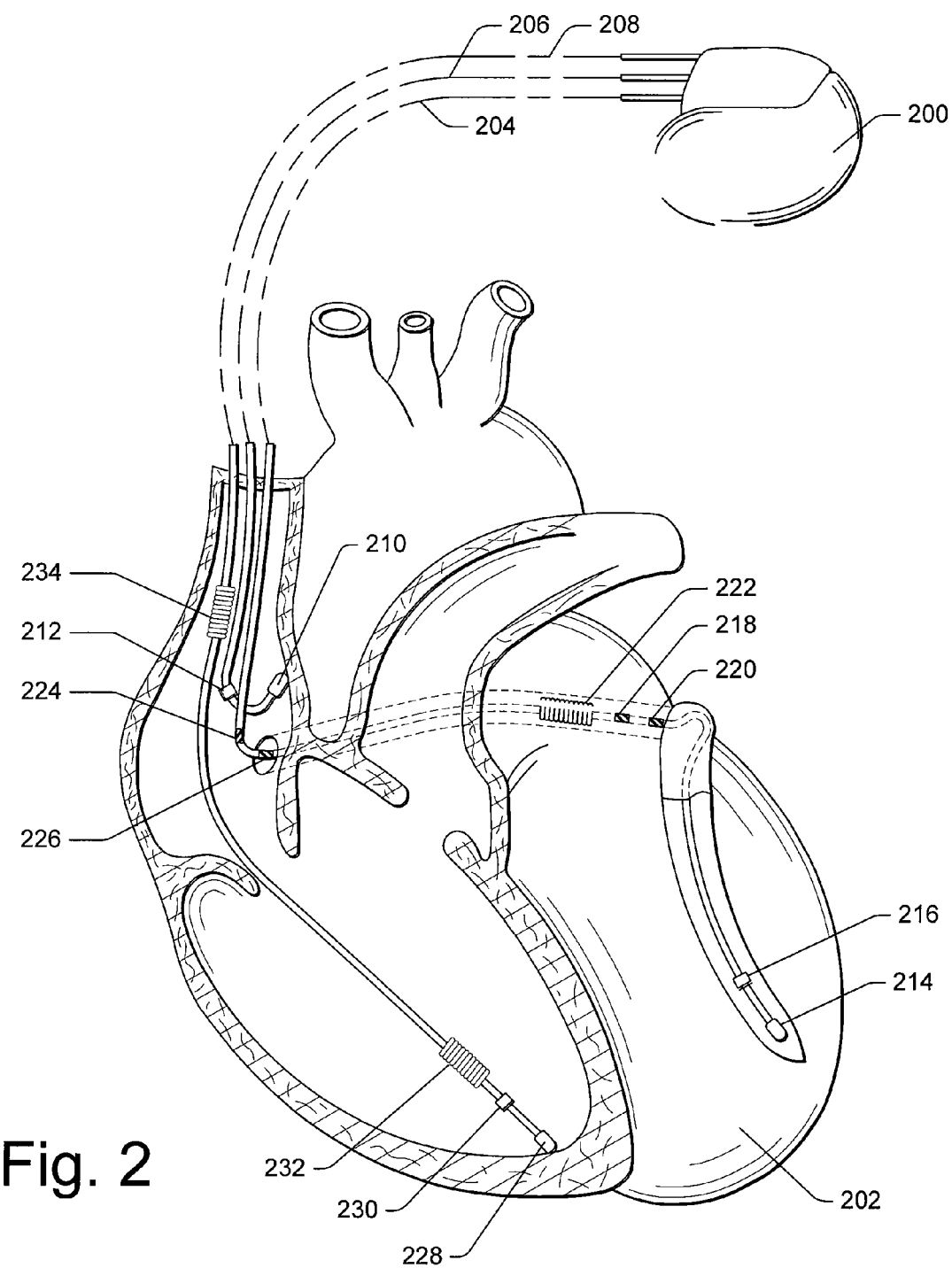
FIG. 2 is a diagram of an exemplary implantable device in relation to a human heart.

Before describing exemplary acquisition of impedances, such as intracardiac impedances, an exemplary implantable device by which the acquisition of impedances can be performed is now described. As shown in FIG. 2, an exemplary implantable stimulation device ("implantable device" 200), in this case an exemplary ICD, is in electrical communication with a patient's heart 202 by way of three leads, 204, 206 and 208, suitable for delivering multi-chamber stimulation and shock therapy. Not every configuration has all of the illustrated electrodes, but a real configuration may include some of the illustrated electrodes and/or even more electrodes than illustrated.

To sense atrial cardiac signals and to provide right atrial chamber stimulation therapy, the implantable device 200 is coupled to an implantable right atrial lead 206, typically having an atrial tip electrode 210 and an atrial ring electrode 212, which typically is implanted in the patient's right atrial appendage. Implantable device 200 is also known as and referred to as a pacing device, a pacing apparatus, a cardiac rhythm management device, or an implantable cardiac stimulation device. Alternatively, the implantable device 200 could be a defibrillator, or cardioverter, or have combined pacing and defibrillation/cardioversion capabilities.

To sense left atrial and ventricular cardiac signals and to provide left chamber pacing therapy, the implantable device 200 is coupled to a "coronary sinus" lead 204 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 204 is designed to receive atrial and ventricular cardiac signals and to deliver left ventricular pacing therapy using a left ventricular (LV) tip electrode 214 and a LV ring electrode 216. Left atrial pacing therapy uses, for example, first and second left atrial (LA) ring electrodes 218 and 220. Shocking therapy can be performed using at least a left atrial (LA) coil electrode 222. For a description of an exemplary coronary sinus lead, see U.S. Pre-Grant Publication No. 20030050681, "A Self-Anchoring Coronary Sinus Lead" (Pianca et al.), and U.S. Pat. No. 5,466,254 to Helland, entitled, "Coronary Sinus Lead with Atrial Sensing Capability," which patent documents are incorporated herein by reference. Coronary sinus lead 204 may also include a pair of right atrial (RA) ring electrodes 224 and 226, which may be used to provide right atrial chamber pacing therapy.

The implantable device 200 is also shown in electrical communication with the patient's heart 202 by way of an implantable right ventricular lead 208, typically having an right ventricular (RV) tip electrode 228, an RV ring electrode 230, an RV coil electrode 232, and a superior vena cava (SVC) coil electrode 234 (also known as a right atrial (RA) coil electrode). Typically, the right ventricular lead 208 is transvenously inserted into the heart 202 so as to place the right ventricular tip electrode 228 in the right ventricular apex so that the RV coil electrode 232 will be positioned in the right ventricle and the SVC coil electrode 234 will be positioned in the superior vena cava. Accordingly, the right ventricular lead 208 is capable of receiving cardiac signals, and delivering stimulation in the form of pacing and shock therapy to the right ventricle.

A single- or multi-vector network, can take simultaneous or quasi-simultaneous impedance measurements over several vectors using any of the electrodes illustrated in FIG. 2, either in pairs or in combinations of three or more electrodes. In one implementation, the terms "simultaneous" and "quasi-simultaneous" used above mean approximately the same as "real-time" and "near real-time," respectively.

Figure 3:
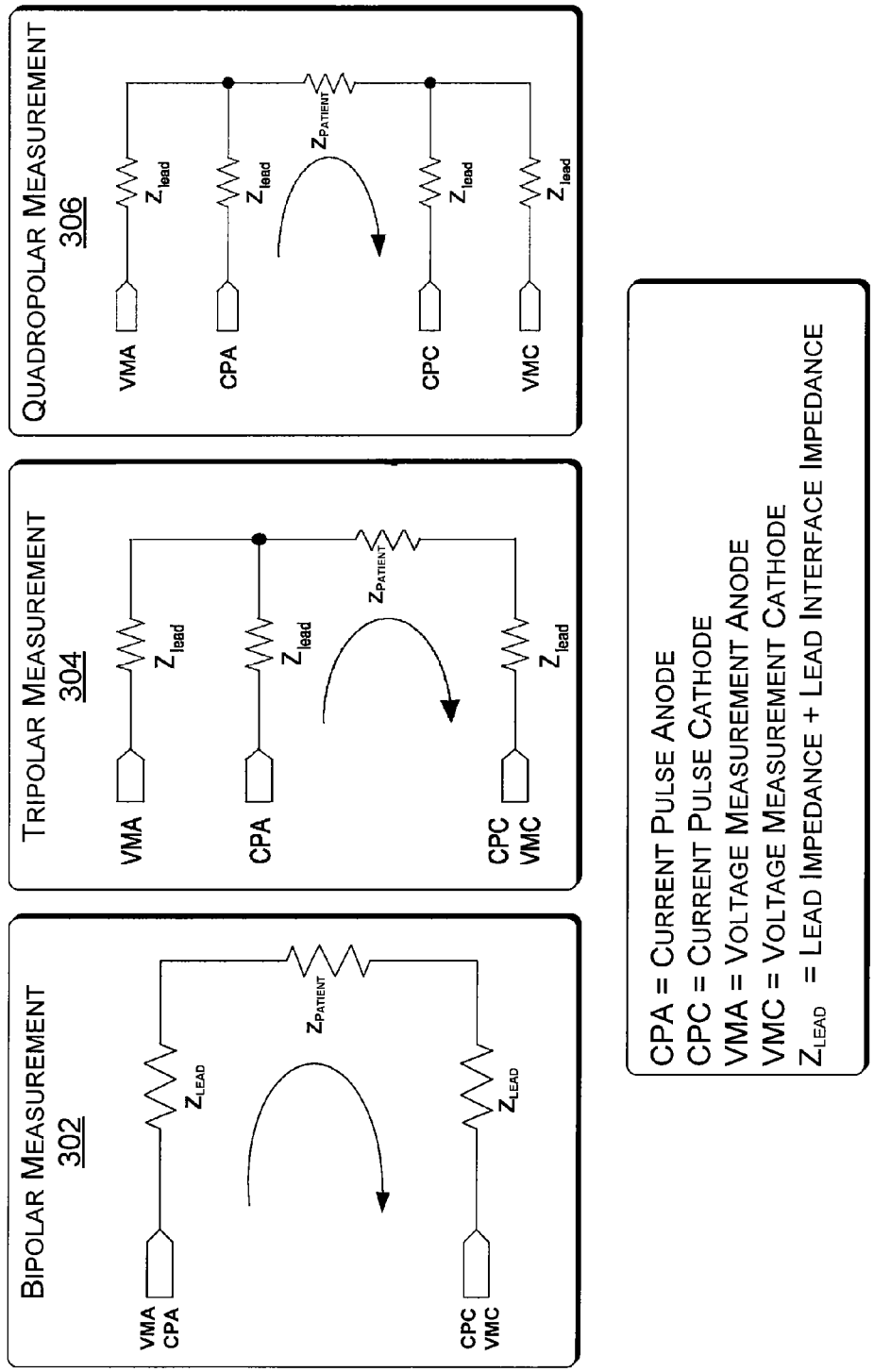
FIG. 3 is a diagram of different impedance measurement electrode configurations.

As shown in FIG. 3, different impedance measurement configurations can be used for each selected vector. In one implementation, an impedance measurement pulse is an injected current waveform 100. The current waveform 100 can be sent across any two leads or lead combinations, per vector. The sensed voltage part of the impedance measurement does not have to be through the same leads as those used for injection of the current waveform 100, but can be selected independently in different available combination. Thus, bipolar 302 (two node measurement), tripolar 304 (three node measurement), and quadrapolar 306 (four node measurement) configurations are all programmable by the exemplary implantable device 200.

Figure 4:
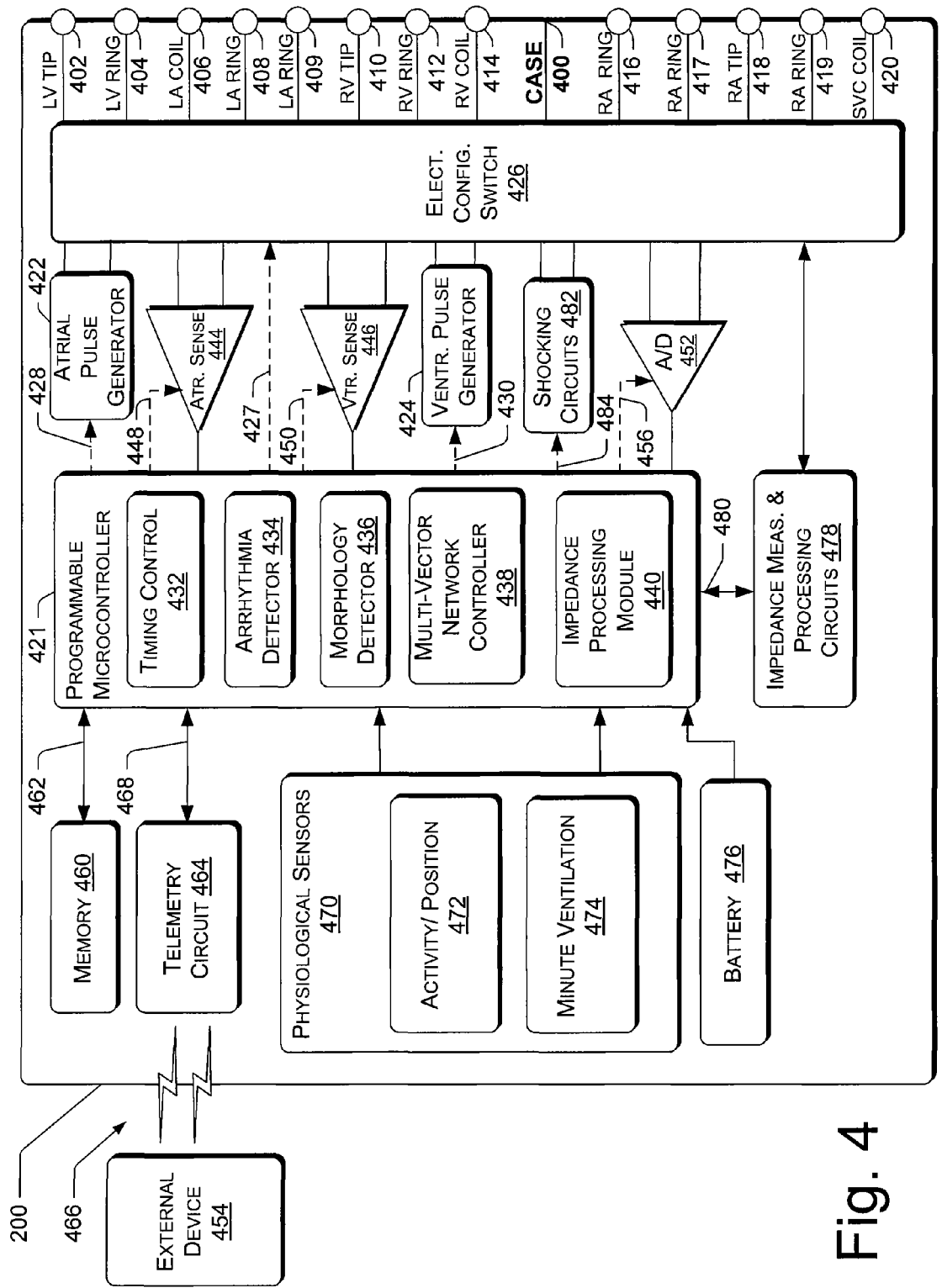
FIG. 4 is a block diagram of the exemplary implantable device of FIG. 2, in greater detail.

FIG. 4 shows an exemplary block diagram depicting various components of the exemplary implantable device 200. The components are typically contained in a case 400, which is often referred to as the "can", "housing", "encasing", or "case electrode", and may be programmably selected to act as the return electrode for unipolar operational modes. The case 400 may further be used as a return electrode alone or in combination with one or more of the coil electrodes 222, 232, 234 for stimulating purposes. The case 400 further includes a connector (not shown) having a plurality of terminals (402, 404, 406, 408, 409, 410, 412, 414, 416, 417, 418, 419, and 420—shown schematically with the names of the electrodes to which they are connected shown next to the terminals), including:

a left ventricular tip terminal (LV TIP) 402 for left ventricular tip electrode 214;

a left ventricular ring terminal (LV RING) 404 for left ventricular ring electrode 216;

a left atrial shocking terminal (LA COIL) 406 for left atrial coil electrode 222;

a left atrial ring terminal (LA RING) 408 for left atrial ring electrode 218;

a left atrial ring terminal (LA RING) 409 for left atrial ring electrode 220;

a right ventricular tip terminal (RV TIP) 410 for right ventricular tip electrode 228;

a right ventricular ring terminal (RV RING) 412 for right ventricular ring electrode 230;

a right ventricular shocking terminal (RV COIL) 414 for RV coil electrode 232;

a right atrial ring terminal (RA RING) 416 for atrial ring electrode 224;

a right atrial ring terminal (RA RING) 417 for right atrial ring electrode 226;

a right atrial tip terminal (RA TIP) 418 for atrial tip electrode 210;

a right atrial ring terminal (RA RING) 419 for atrial ring electrode 212; and a SVC shocking terminal (SVC COIL) 420 for right atrial SVC coil electrode 234.

An exemplary implantable device 200 may include a programmable microcontroller 421 that controls various operations of the implantable device 200, including cardiovascular monitoring, hemodynamic monitoring, and cardiovascular stimulation therapy. Microcontroller 421 includes a microprocessor (or equivalent control circuitry), RAM and/or ROM memory, logic and timing circuitry, state machine circuitry, and I/O circuitry.

The exemplary implantable device 200 may further include an atrial pulse generator 422 and a ventricular pulse generator 424 that generate pacing stimulation pulses for delivery by the right atrial lead 206, the coronary sinus lead 204, and/or the right ventricular lead 208 via an electrode configuration switch 426. The electrode configuration switch 426 may include multiple switches for connecting the desired electrodes to the appropriate I/O circuits, thereby providing complete electrode programmability. Accordingly, switch 426, in response to a control signal 427 from the microcontroller 421, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 422 and 424 may include dedicated, independent pulse generators, multiplexed pulse generators, or shared pulse generators. The pulse generators 422 and 424 are controlled by the microcontroller 421 via appropriate control signals 428 and 430, respectively, to trigger or inhibit the stimulation pulses.

Microcontroller 421 is illustrated as including timing control circuitry 432 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 421 may also implement an arrhythmia detector 434, a morphology detector 436, a multi-vector network controller 438, and an impedance processing module 440. The microcontroller 421 may process input from physiological sensors 470, such as accelerometers of an activity/position module 472, and a minute ventilation module 474, etc., The components 434, 436, 438, and 440 may be implemented in hardware as part of the microcontroller 421, or as software/firmware instructions programmed into an implementation of the implantable device 200 and executed on the microcontroller 421 during certain modes of operation. Although not shown, the microcontroller 421 may further include other dedicated circuitry and/or firmware/software components that assist in monitoring various conditions of the patient's heart and managing pacing therapies.

Atrial sensing circuits 444 and ventricular sensing circuits 446 may also be selectively coupled to the right atrial lead 206, coronary sinus lead 204, and the right ventricular lead 208, through the switch 426 to detect the presence of cardiac activity in each of the four chambers of the heart. The sensing circuits 444 and 446 may include dedicated sense amplifiers, multiplexed amplifiers, or shared amplifiers. Switch 426 determines the "sensing polarity" of the cardiac signal by selectively closing the appropriate switches. In this way, the clinician may program the sensing polarity independent of the stimulation polarity.

Each sensing circuit 444 and 446 may employ one or more low power precision amplifiers with programmable gain and/or automatic gain control, bandpass filtering, and a threshold detection circuit to selectively sense the cardiac signal of interest. The automatic gain control enables the exemplary implantable device 200 to sense low amplitude signal characteristics of atrial or ventricular fibrillation.

The outputs of the atrial and ventricular sensing circuits 444 and 446 are connected to the microcontroller 421 which, in turn, is able to trigger or inhibit the atrial and ventricular pulse generators 422 and 424 in a demand fashion in response to the absence or presence of cardiac activity in the appropriate chambers of the heart. The sensing circuits 444 and 446 receive control signals from the microcontroller 421 over signal lines 448 and 450 to control, for example, the gain and the timing of blocking circuitry (not shown) optionally coupled to the inputs of the sensing circuits 444, 446.

Cardiac signals, including signals involved in impedance measurements, are supplied to an analog-to-digital (ND) data acquisition system 452, which is configured to acquire these signals, convert the raw analog data into a digital signal, and store the digital signals for later processing and/or telemetric transmission to an external device 454. The data acquisition system 452 is coupled to the right atrial lead 206, the coronary sinus lead 204, and the right ventricular lead 208 through the switch 426 to process signals across any pair of desired electrodes.

The data acquisition system 452 is coupled to the microcontroller 421, or other detection circuitry, to assist in detecting an evoked response from the heart 202 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 421 detects a depolarization signal during a window following a stimulation pulse, the presence of which indicates that capture has occurred. The microcontroller 421 enables capture detection by triggering the ventricular pulse generator 424 to generate a stimulation pulse, starting a capture detection window using the timing control circuitry 432 within the microcontroller 421, and enabling the data acquisition system 452 via control signal 456 to sample the cardiac signal that falls in the capture detection window and, based on the amplitude, determines if capture has occurred.

The microcontroller 421 is further coupled to a memory 460 by a suitable data/address bus 462. The programmable operating parameters used by the microcontroller 421 are stored in memory 460 and used to customize the operation of the exemplary implantable device 200 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 202 within each respective tier of therapy.

The operating parameters of the exemplary implantable device 200 may be non-invasively programmed into the memory 460 through a telemetry circuit 464 in telemetric communication via communication link 466 with the external device 454, such as a programmer, local transceiver, or a diagnostic system analyzer. The microcontroller 421 can activate the telemetry circuit 464 with a control signal 468. The telemetry circuit 464 allows intracardiac electrograms and status information relating to the operation of the exemplary implantable device 200 (as contained in the microcontroller 421 or memory 460) to be sent to the external device 454 through an established communication link 466.

The physiological sensors 470 referred to above can further include, for example, "rate-responsive" sensors that adjust pacing stimulation rates according to the exercise state of the patient. Accordingly, the microcontroller 421 responds by adjusting the various pacing parameters (such as rate, etc.) at which the atrial and ventricular pulse generators 422 and 424 generate stimulation pulses.

The physiological sensors 470 may include mechanisms and sensors to detect bodily movement (472), minute ventilation 474, changes in blood pressure, changes in cardiac output, changes in the physiological condition of the heart, diurnal changes in activity (e.g., detecting sleep and wake states), G-force acceleration of the ICD case 400, length of the cardiac QT interval, blood oxygen saturation, blood pH, changes in temperature, respiration rate, and QRS wave duration. While shown as being included within the exemplary implantable device 200, the physiological sensor(s) 470 may also be external to the exemplary implantable device 200, yet still be implanted within or carried by the patient, e.g., a blood pressure probe. Examples of physiological sensors external to the case 400 that may be deployed by implantable device 200 include sensors that, for example, sense respiration activities, $O_2$ saturation, evoked response, pH of blood, and so forth.

The illustrated physiological sensors 470 include one or more activity/position sensors 472 (e.g., 1D or 3D accelerometers, movement sensors, etc.) to detect changes in the patient's position. The activity/position sensors 472 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up).

In one configuration, accelerometer output signal is band-pass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 474 may also be included in the physiological sensors 470 in order to sense rate and depth of breathing. Minute ventilation can be measured as the total volume of air that moves in and out of a patient's lungs in a minute. The MV sensor 474 may use impedance measuring and processing circuits 478 to sense air movement by measuring impedance across the chest cavity.

The impedance measuring and processing circuits 478 communicate with the microcontroller 421, e.g., via control signals 480 and can be used for obtaining many types of bodily and intracardiac impedances, including a network of single- or multi-vector impedance measurements. Such impedance measurements can be used for trending many kinds of physiological variables, and can also be used for detection of air movement in and out of the lungs, lead impedance surveillance during acute and chronic phases for proper lead positioning or dislodgement; detecting operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 478 may be coupled to the switch 426 so that any desired electrode may be used, and networks of vectors can be selected by the multi-vector network controller 438.

The exemplary implantable device 200 additionally includes a battery 476 that provides operating power to all of the components shown in FIG. 4. The battery 476 is capable of operating at low current drains for long periods of time (e.g., less than 10 µA), and is capable of providing high-current pulses (for capacitor charging) when the patient requires a shock pulse (e.g., in excess of 10 A, at voltages above 500 V, for periods of 2-20 microseconds). The battery 476 also desirably has predictable discharge characteristics so that elective replacement time can be detected. As one example, the exemplary implantable device 200 employs lithium/silver vanadium oxide batteries.

The exemplary implantable device 200 can further include magnet detection circuitry (not shown), coupled to the microcontroller 421, to detect when a magnet is placed over the exemplary implantable device 200. A magnet may be used by a clinician to perform various test functions of the exemplary implantable device 200 and/or to signal the microcontroller 421 that an external programmer (e.g., 454) is in place to receive or transmit data to the microcontroller 421 through the telemetry circuits 464.

The microcontroller 421 further controls a shocking circuit 482 via a control signal 484. The shocking circuit 482 generates shocking pulses of low (e.g., up to 0.5 joules), moderate (e.g., 0.5-10 joules), or high energy (e.g., 11-40 joules), as selected by the microcontroller 421. Such shocking pulses are applied to the patient's heart 202 through at least two shocking electrodes selected, for example, from the left atrial coil electrode 222, the RV coil electrode 232, and/or the SVC coil electrode 234. As noted above, the case 400 may act as an active electrode in combination with the RV coil electrode 232, or as part of a split electrical vector using the SVC coil electrode 234 or the left atrial coil electrode 222 (i.e., using the RV coil electrode 232 as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 421 is capable of controlling the synchronous or asynchronous delivery of the shocking pulses.

More generally, the exemplary implantable device 200 can be programmed to stimulate different sets of vascular and cardiac muscles through the same lead/electrode system. The exemplary implantable device 200 can be programmed to vary the output voltage of various pulses to effectively stimulate different muscles of the heart and blood vessels, even though the physical placement of leads and electrodes does not change.

Figure 5:
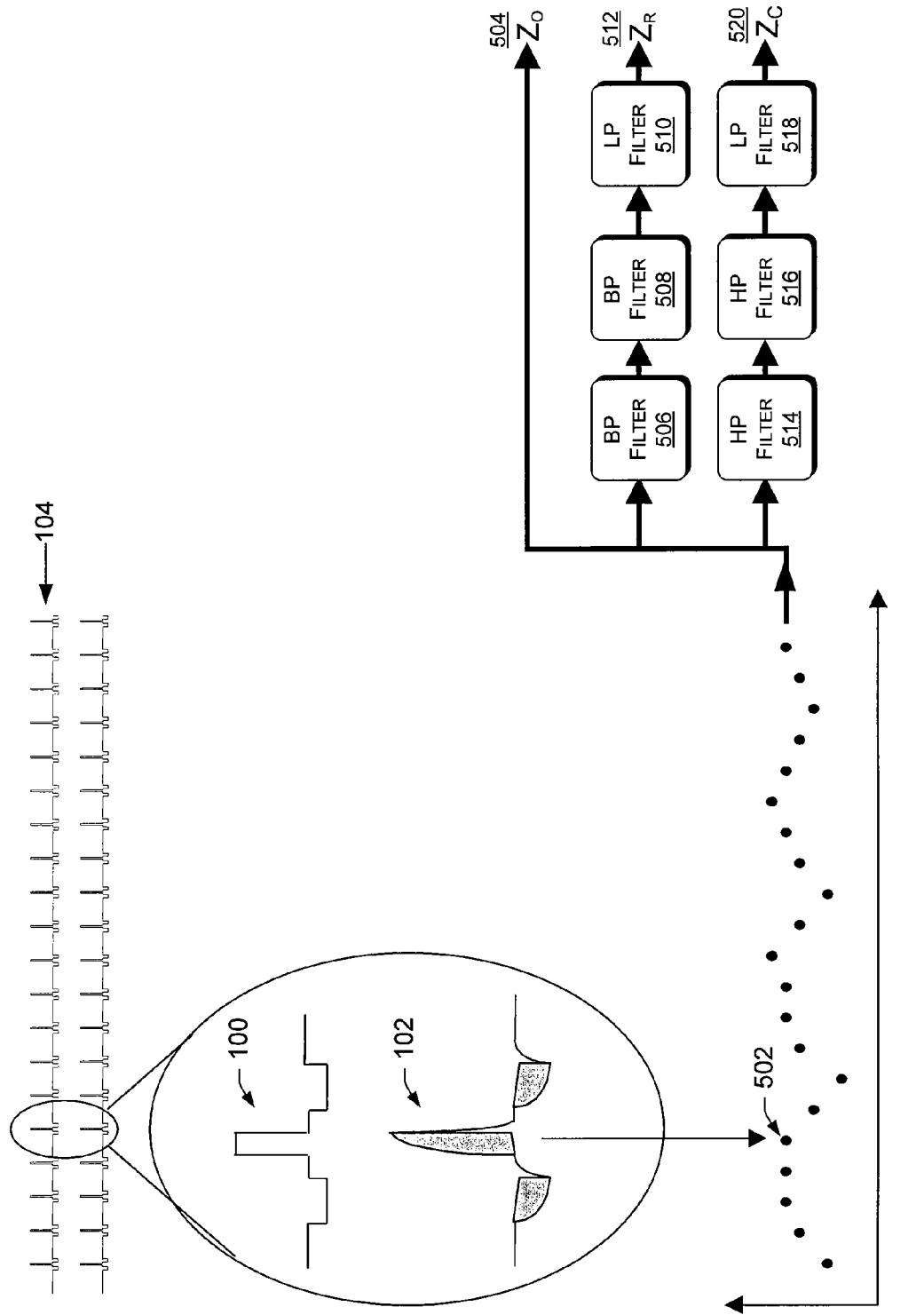
FIG. 5 is a diagram of exemplary types of impedances obtainable using the exemplary pulse waveforms of FIG. 1.

FIG. 5 shows exemplary types of impedance measurements that can be obtained from the exemplary areal (area-based) technique described above with respect to FIG. 1. As described above, the areal technique derives an impedance measurement for each selected vector by finding the areas under each of the injected and sensed pulse waveforms, and dividing the areas representing voltage by the areas representing current to obtain an impedance result 502. With relatively little processing, the integration process just described provides a "raw" impedance measurement $Z_o$ 504, which can be useful for determining extra- or intra-cardiac impedances and examining conditions such as pulmonary edema. From $Z_o$ 504, other component impedances may be derived. That is, the raw impedance measurement $Z_o$ 504 includes impedance components caused by the breathing cycle and the cardiac cycle, with respiratory cycle waves and cardiac cycle waves being superimposed on the underlying tissue impedance.

By applying selected bandpass filters 506 and 508 and low pass filter 510 to the raw impedance $Z_o$ 504 the respiration component $Z_r$ 512 can be filtered out for use, for example, in tracking respiration rate and depth, sleep apnea, and CHF conditions, etc. Likewise, by applying selected high pass filters 514 and 516 and low pass filter 518 to the raw impedance $Z_o$ 504, the cardiac component $Z_c$ 520 can be filtered out for use, for example, in tracking various hemodynamic parameters.

Figure 6:
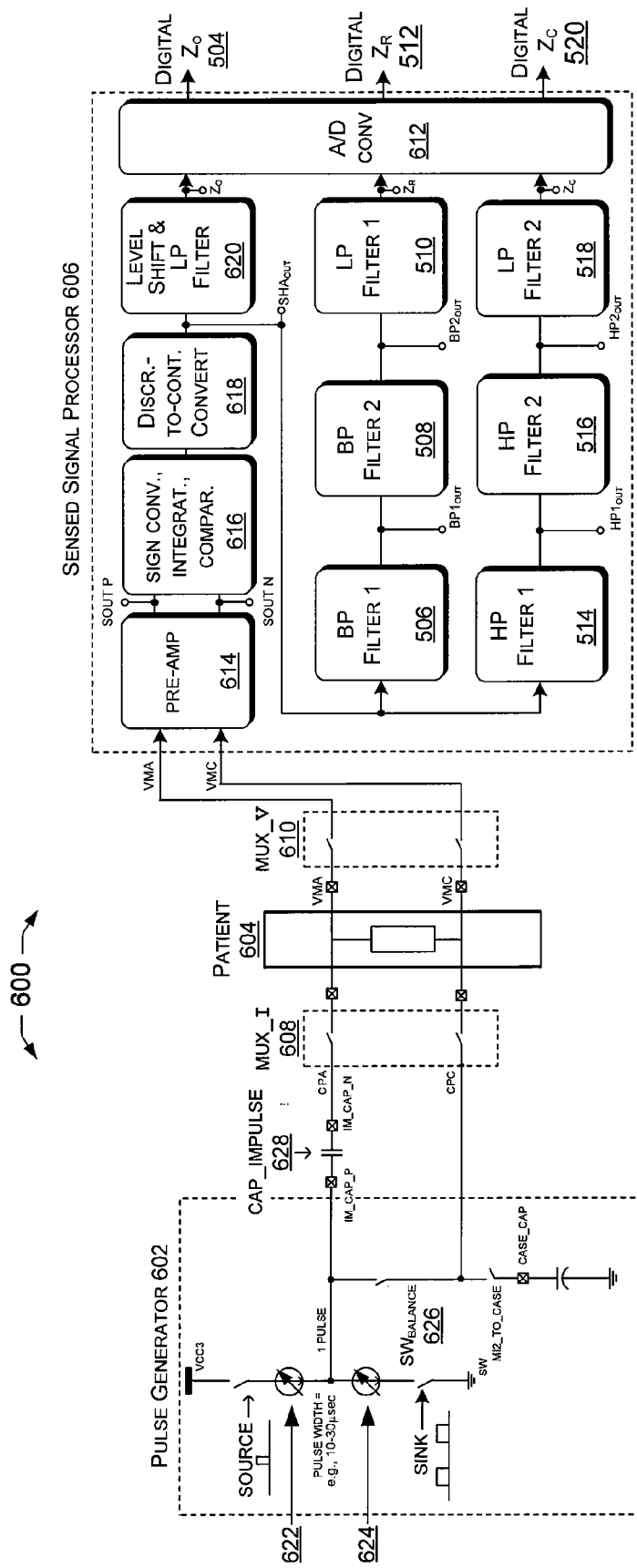
FIG. 6 is a block diagram of an exemplary impedance measurement circuit architecture.

FIG. 6 shows an exemplary impedance measurement circuit architecture 600, including the filter components shown in FIG. 5 in greater detail. The illustrated architecture 600 is just one example configuration, other configurations are also possible. In one implementation, the exemplary impedance measurement architecture 600 includes a pulse generator 602 for generating a pulse waveform 100, in this case a current waveform, for injection into a patient 604 and a sensed signal processor 606 for processing resultant waveforms 102, in this case voltage waveforms, from the patient 604. An injection (current pulse) mutliplexer 608 implements the single- or multi-vector aspect of signal injection by determining a first set of electrodes for injecting the exemplary waveform 100. Likewise, a sensing (voltage measurement) multiplexer 610 implements the aspect of signal sensing by determining a second set of electrodes for sensing the resulting voltage waveforms 102.

The sensed signal processor 606 typically consists of pre-amplification circuitry, switched capacitor filters, and an analog to digital converter 612. In one implementation, the voltage signal from the voltage measurement multiplexer 610 is processed by several voltage measurement lines or paths. The illustrated sensed signal processor 606 is able to obtain at least the three different impedance signals introduced above with respect to FIG. 5, that is, low frequency raw impedance $Z_o$ 504, respiration impedance $Z_r$ 512, and cardiac impedance $Z_c$ 520. Each measurement can be activated separately or simultaneously.

A digital form of raw impedance $Z_o$ 504 may be obtained. First, the sensed signal, i.e., the tri-phasic voltage waveform 102 from the voltage measurement multiplexer 608, is sent to a preamplifier 614. The next stage is embodied in a sign conversion and integration module 616. At this stage, the signal is converted into an absolute value and then integrated over time. Using the integration process instead of conventional instantaneous "snapshot" measurements of impedance components such as pure resistance produces results that are more noise-free and more accurate than the conventional techniques.

A discrete to continuous signal conversion module 618 is then applied to the signal. At this point in the architecture 600, the signals for low frequency impedance $Z_o$ 504, respiration impedance $Z_r$ 512, and cardiac impedance $Z_c$ 520 are extracted separately by different filter paths, as summarized in FIG. 5. To obtain the low frequency impedance $Z_o$ 504, the signal is sent to a level shift and low pass filter module 620, and then to the analog to digital converter 612.

A digital form of the respiration impedance $Z_r$ 512 may be obtained by tapping the analog signal from the input of the level shift and low pass filter module 620, and feeding the signal to a line consisting of bandpass filters 506 and 508 and a low pass filter 510. The signal is then fed to the analog to digital converter 612 to obtain digital $Z_r$ 512.

A digital form of the cardiac impedance $Z_c$ 520 may likewise be obtained by tapping the analog signal from the input of the level shift and low pass filter module 620, and feeding the signal to a line consisting of high pass filters 514 and 516 and a low pass filter 518. The signal is then fed to the analog to digital converter 612 to obtain digital $Z_c$ 520.

In one implementation, the pulse generator 602 consists of two timing-controlled current generators 622 and 624 with programmable magnitude. The first current generator 622 sources current, the other current generator 624 sinks the current. As part of the charge and voltage balancing process, the switch $SW_{Balance}$ 626 is used to discharge the external capacitor Cap_Impulse 628 after each generated impulse. The pulse rate is programmable.

Components of the impedance measurement architecture 600 may be distributed across the impedance measuring & processing circuits 478 (FIG. 4) and the impedance processing module 440 (FIG. 4), the distribution of components depending on implementation. That is, the exemplary impedance measurement architecture 600 may be implemented in hardware, software, or combinations thereof. For example, the exemplary impedance measurement architecture 600 may be implemented in hardware as part of the microcontroller 421 and/or as hardware integrated into the fabric of the exemplary implantable device 200; or as software/firmware instructions programmed into an implementation of the implantable device 200 and executed on the microcontroller 421 during certain modes of operation. In one implementation, the microcontroller 421 could process the impedance at several time points. The impedance trend seen at these various time points could be used to determine physiological parameters or patient conditions, such as heart enlargement, heart failure, pulmonary edema.

In one implementation, the preamplifier 614 is included in the impedance measuring & processing circuits 478. The pulse generator 602 can be implemented in the impedance processing module 440 as can some of the other components of the sensed signal processor 606.

Although the illustrated version of the impedance measurement circuit architecture 600 injects a current pulse waveform 100 and senses a voltage pulse waveform 102, other implementations can inject a voltage waveform and sense a current waveform.

Figure 7:
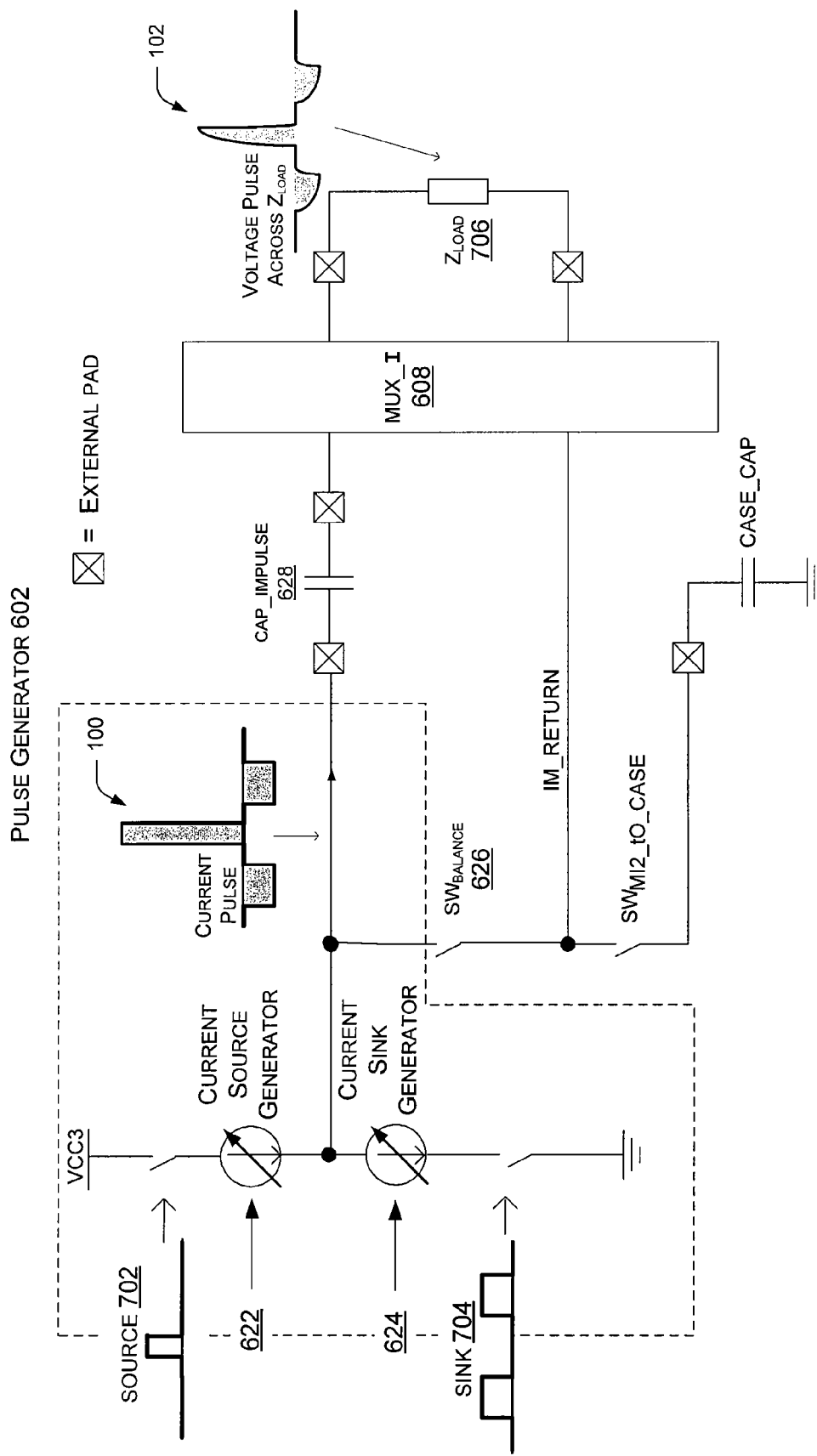
FIG. 7 is a block diagram of the pulse generator shown in FIG. 6, in greater detail.

FIG. 7 shows the pulse generator 602 in relation to pulse waveforms as they exist at different points in the generation process. A source signal 702 is fed to the current source generator 622 to produce the positive phase 106 of the current pulse waveform 100. Multiple square waves typically constitute the sink signal 704 sent to the current sink generator 624 to produce the negative phases 108 and 108' of the current pulse waveform 100. The relative widths and magnitudes of the source signal 702 and the sink signal 704 determine whether the current pulse waveform has symmetric properties or asymmetric properties, to be discussed further below.

Because in one implementation the source signal 702 and sink signal 704 are simple square waves and their relative widths and magnitudes are known, and because it is easy to track the number of pulses injected, the area of the injected current pulse waveforms 100 is known or easily calculated and does not have to be calculated by the sensed signal processor 606. Thus, the sensed signal processor 606 only has to calculate the area of sensed voltage pulse waveforms 102. As shown, the voltage pulse waveform 102 is the voltage signal that results when the current pulse waveform 100 is sent in a circuit through the impedance load $Z_{LOAD}$ 706 of a bodily tissue path.

Figure 8:
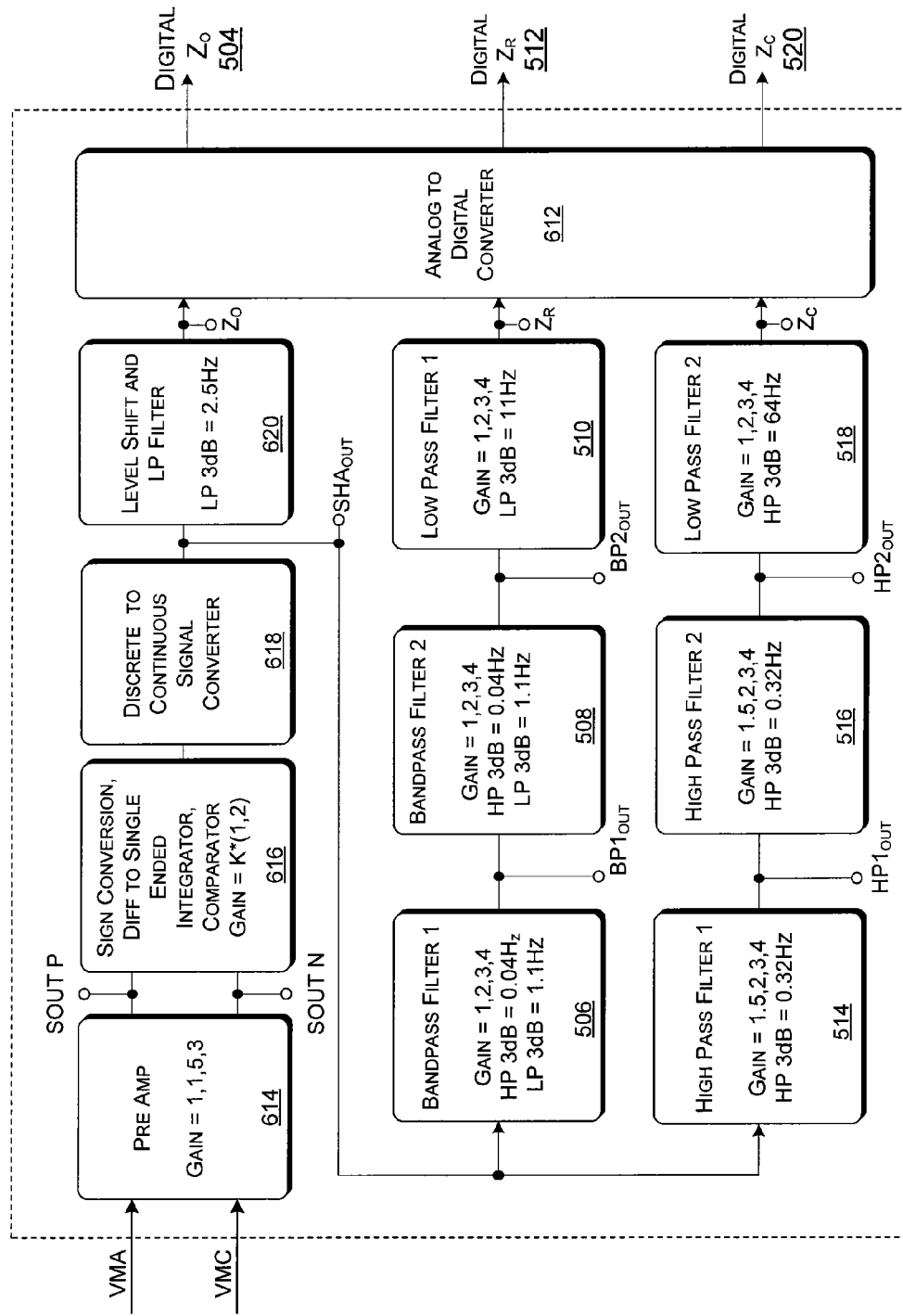
FIG. 8 is a block diagram of the sensed signal processor shown in FIG. 6, in greater detail.

FIG. 8 shows another view of the sensed signal processor 606 of FIG. 6. Some components will be shown in greater detail in succeeding figures. In FIG. 8, exemplary filtering values are shown for some of the components. For example, the low frequency impedance $Z_o$ 504 can be obtained using the level shift and low pass filter 620 having the values shown. Likewise, the respiration impedance $Z_r$ 512 can be obtained by tapping the analog signal from the input of the level shift and low pass filter module 620, as mentioned above, and feeding the signal to a line consisting of bandpass filters 506 and 508 and low pass filter 510 having the illustrated values. The cardiac impedance $Z_c$ 520 can be extracted by tapping the analog signal from the input of the level shift and low pass filter module 620, and feeding the signal to a line consisting of high pass filters 514 and 516 and a low pass filter 518 having the illustrated values.

Figures 9, 10:
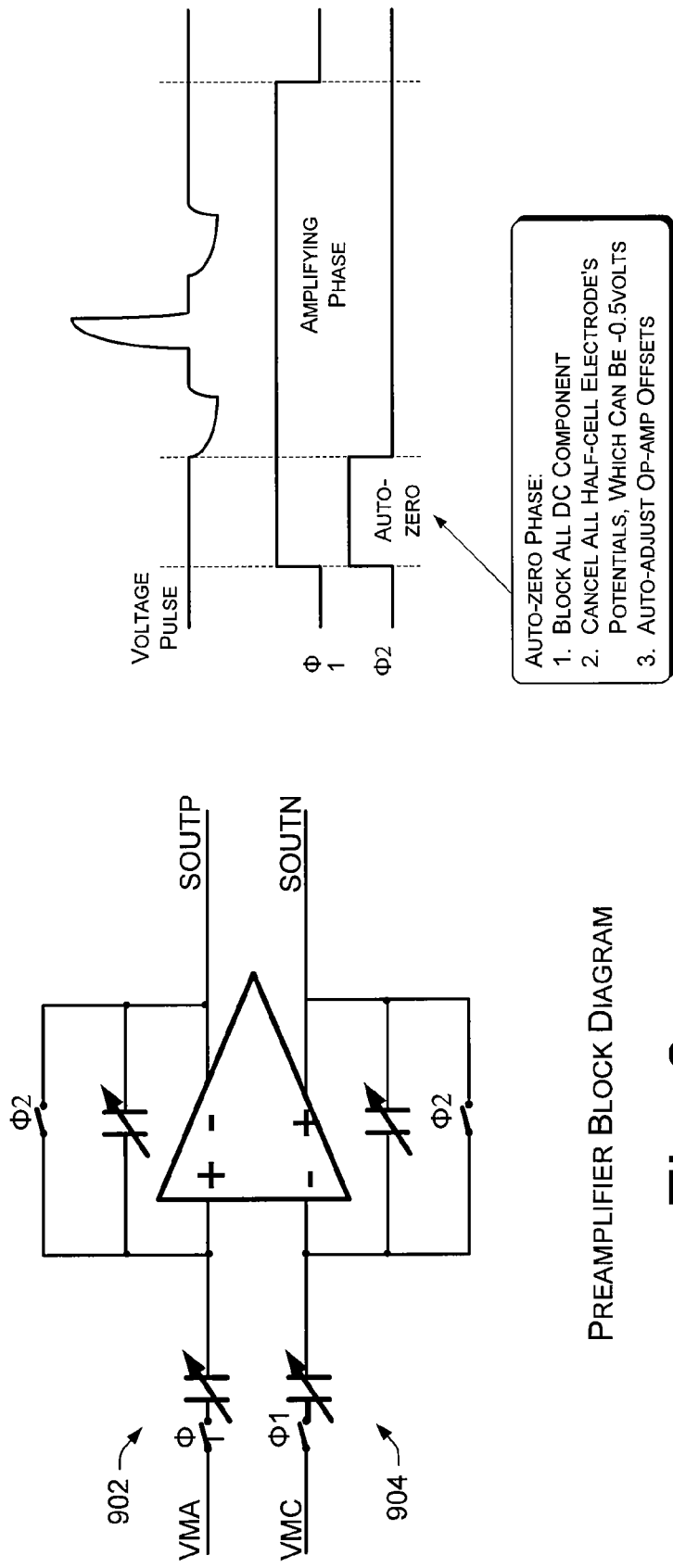
FIG. 9 is a block diagram of the preamplifier shown in FIGS. 6 and 8.
FIG. 10 is a timing diagram for the preamplifier of FIG. 9.

FIG. 9 shows the exemplary preamplifier 614 of FIGS. 6 and 8 in greater detail. In one configuration, a switch capacitor operational amplifier amplifies the differential input signals received from the voltage measurement multiplexer 610. The signals designated by VMA and VMC that are input to the preamplifier 614 (via the voltage measurement multiplexer 610) are voltages sensed directly from electrodes in direct contact with bodily tissue, that is, the received voltage waveforms 102 are the raw voltages as sensed from bodily tissue. The preamplifier 614 outputs a positive signal (SOUTP) and a negative signal (SOUTN) to the integrator 616.

In one implementation, switched blocking capacitors 902 and 904 minimize artifacts that might be introduced by polarization potentials or by slowly varying voltages introduced by the capacitive and resistive nature of electrode/electrolyte interfaces.

FIG. 10 shows a timing diagram for the operation of the exemplary preamplifier 614. In an auto zero phase, the preamplifier 614 blocks DC signals, i.e., DC components, and cancels half-cell potentials, which can be, e.g., −0.5 volts. During the auto zero phase the preamplifier 614 may auto-adjust or remove op-amp offsets. In an amplification phase, the preamplifier 614 amplifies the differential input signals received from the voltage measurement multiplexer 610. In one implementation, the preamplifier gain is programmable.

Figures 11, 12:
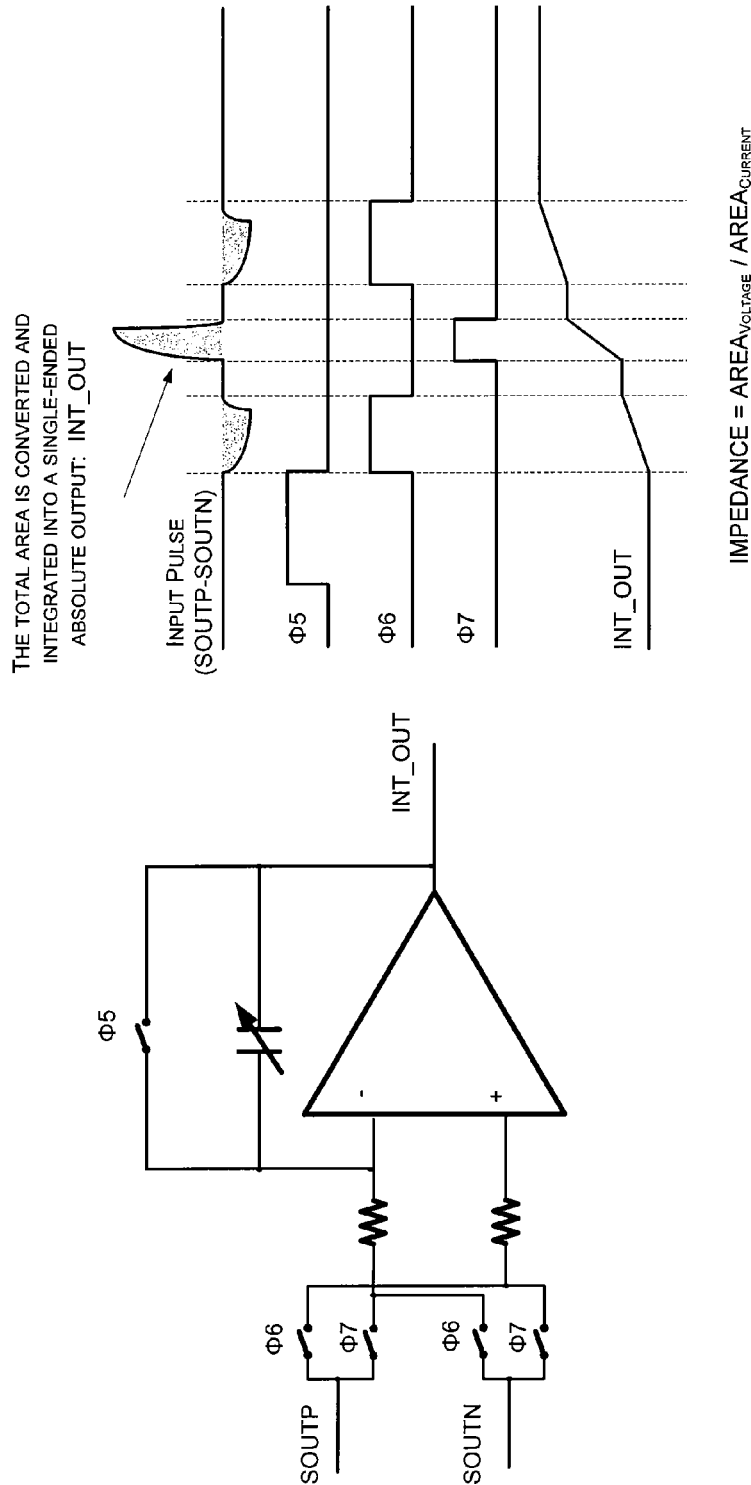
FIG. 11 is a block diagram of the exemplary integrator shown in FIGS. 6 and 8.
FIG. 12 is a timing diagram for the integrator shown in FIG. 11.

FIG. 11 shows an exemplary implementation of the integrator, that is, the sign-converting differential-to-single-ended integrator/comparator 616 that rectifies and integrates the sensed signal. The differential signal received from between the two outputs of the preamplifier 614, SOUTP and SOUTN, is still a tri-phasic pulse. The integrator 616 obtains an absolute value of the voltage pulse waveform and integrates the absolute area given by this tri-phasic voltage pulse.

The exemplary method of computing impedance by dividing the integration output (i.e., the area under the rectified signal) by the corresponding area under the injected signal has the advantage of eliminating the need for fast digital sampling and is more tolerant of small phase delays between the injected and sensed signals. Additionally, the method lends itself to CMOS realization using low-value switched capacitor solutions. Indeed, given the short duration of the injected signal, the values of the components used in the integrator 616 can be realized in CMOS implementations.

FIG. 12 shows a timing diagram of the operation of the integrator 616. The beginning and ending edges of each phase of the voltage pulse waveform determine the various parts of an integration process, wherein the three phases of the tri-phasic waveform, for instance, are separately integrated (and summed) into a single-ended absolute output, e.g., INT_OUT. In one implementation, this stage also compares the obtained area value of the entire voltage pulse waveform with the known area value of the injected current waveform. This yields an impedance value (when the area representing voltage is divided by the area representing current).

Figures 13, 14:
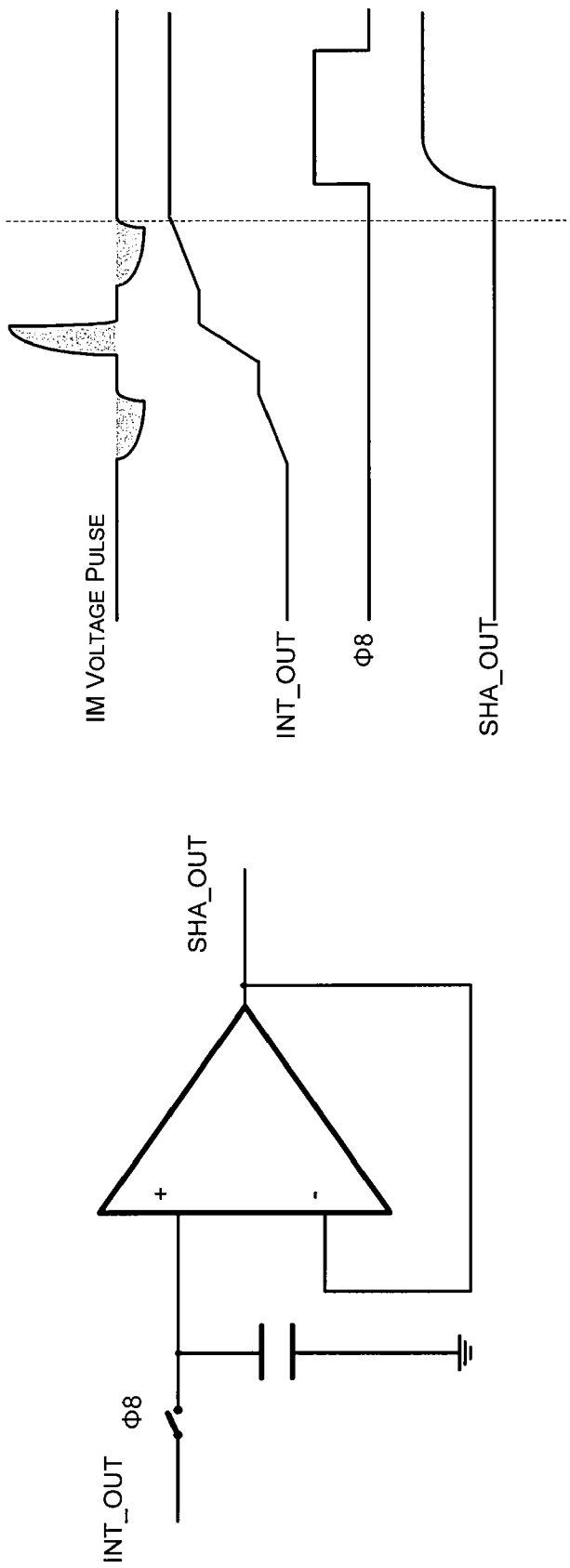
FIG. 13 is a block diagram of the exemplary discrete to continuous signal converter shown in FIGS. 6 and 8.
FIG. 14 is a timing diagram for the discrete to continuous signal converter of FIG. 13.

FIG. 13 shows an exemplary implementation of the discrete-to-continuous signal converter 618. This stage converts the discrete output of the integrator 616 into a more useful continuous signal. In one implementation, the conversion to a smoother signal is timed to occur after the integration, as shown in FIG. 14.

Figure 15:
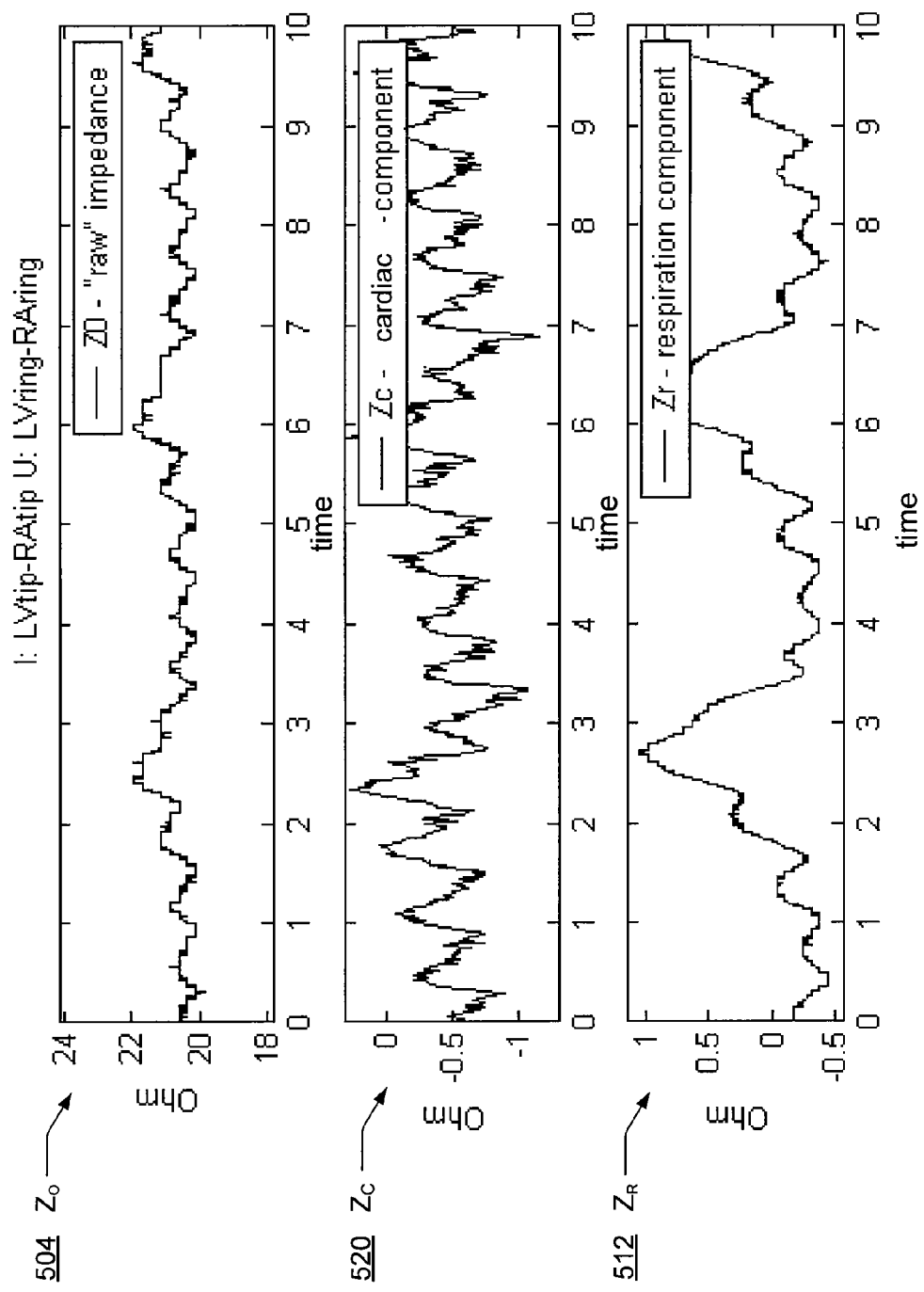
FIG. 15 is a diagram of the exemplary impedances introduced in FIG. 5.

FIG. 15 shows graphical examples of impedance measurements $Z_o$ 504, $Z_c$ 520, and $Z_r$ 512 made over time, e.g., as obtained by the impedance measurement circuit architecture 600 of FIG. 6. This example shows a current impulse waveform 100 that has been injected via only one vector, between left ventricular tip electrode 214 and right atrial tip electrode 210. In a quadrapolar measurement (306) configuration, the resulting voltage waveforms 102 are sensed between left ventricular ring electrode 216 and right atrial ring electrode 212. As illustrated, cardiac and respiratory wave effects on impedance (i.e., $Z_c$ 520 and $Z_r$ 512) are superimposed on the raw impedance wave $Z_o$ 504. When $Z_c$ 520 and $Z_r$ 512 are extracted from $Z_o$ 504, the underlying tissue-path impedance for the selected vector remains, which is useful for distinguishing tissues or detecting congestive heart failure conditions or pulmonary edema, etc.

Exemplary Waveforms

The exemplary waveforms 100, as introduced with respect to FIG. 1, are multi-phasic and both charge-balanced and voltage-balanced. Each waveform 100 has a total duration less than the charging time constant of the electrode-electrolyte interfaces used to inject and sense the signals. These time constants are typically in the range of a few milliseconds. In one implementation, the duration of waveform 100 is less than 1 millisecond. This waveform feature is helpful to minimizing polarizations effects at these electrode-electrolyte interfaces. Other features of the exemplary waveforms 100 include symmetric or asymmetric phase duration, decreasing phase amplitudes, and alternating phase signs. Each waveform 100 typically has null durations in between phases to provide time for completely processing information from one phase before the next phase begins. Implementations of the waveform 100 that have square wave pulses (or rectangular wave pulses) contain a great deal of high frequency content. Near sinusoidal implementations of the waveform 100 may contain less high frequency content than the square wave versions.

The features of exemplary waveforms 100 just enumerated provide numerous advantages, including: eliminating the need for fast digital sampling, minimizing artifacts introduced in the measurement process, increased tolerance of small phase delays between injected and sensed signals. The exemplary waveforms 100 lend themselves to CMOS realization using low-value switched capacitor solutions. Further, the wide frequency spectrum of the injected signal can be used to implement algorithms that differentiate tissues based on their frequency response, and/or phase delay. The very low duty-cycle of the exemplary waveforms 100 make them safer for patients. The reduced duty-cycle brings the injected charge and the root-mean-square value of the injected signal well below levels that could be perceived by the patient or that could induce adverse events.

In one implementation, the exemplary impedance measurement circuit architecture 600 can deliver current pulse waveforms of two different tri-phasic shapes, asymmetrical or symmetrical. Other implementations can provide alternative multi-phasic waveform shapes also, for example, as shown below in FIG. 22. Further, in one variation, at least some of the negative phases of a multi-phasic waveform have the same duration as at least some of the positive phases of the waveform. In another variation, none of the negative phases of the multi-phasic waveform have the same duration as the positive phases. In yet another variation, the duration of at least some of the negative phases varies in relation to changes in the duration of one or more of the positive phases. In these various implementations, each exemplary waveform is charge-balanced, but additionally each waveform is also voltage-balanced, a feature that provides no build-up of non-zero-mean voltages at electrode interfaces caused by a net imbalance between net positive and net negative phases of the waveform. Such non-zero-mean voltages would be detrimental to accurate electrogram sensing and ECG acquisition. Since in a current-injection implementation the waveforms are charge-balanced and voltage-balanced, there is no net charge or current residue transferred by the injected current and no net voltage imbalance between sensing leads.

Figure 16:
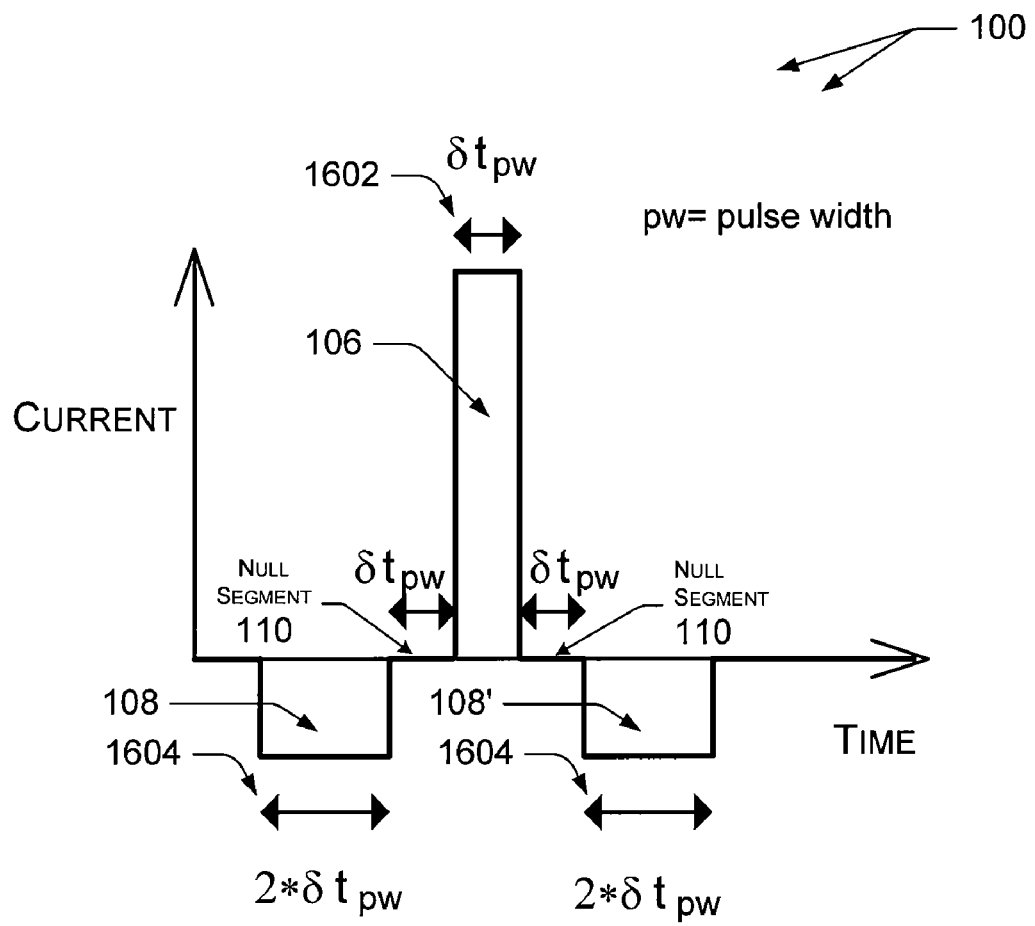
FIG. 16 is a diagram of an exemplary asymmetric tri-phasic pulse waveform.

FIG. 16 shows the asymmetric waveform 100 introduced in FIG. 1. The waveform shape is defined to be asymmetrical if the width 1602 of the positive phase 106 of the pulse waveform 100 is anything but equal to the width 1604 of the negative phase(s) of the pulse waveform 100. Regardless of symmetry, in every tri-phasic pulse waveform 100, the two negative phases 108 of the pulse waveform 100 are designed to balance the positive phase 106 of the pulse waveform 100. This results in no DC component between the injection leads.

Figure 17:
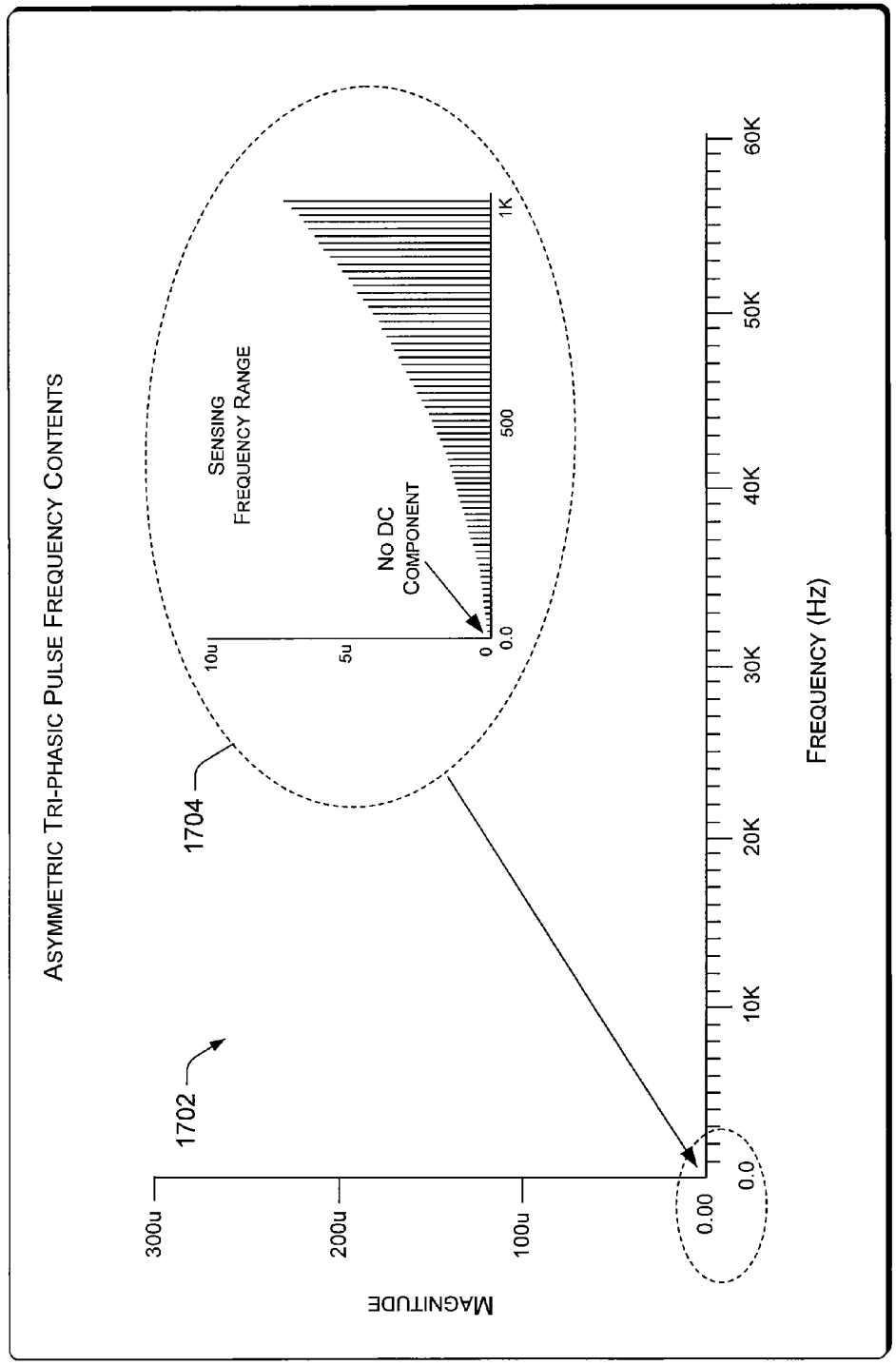
FIG. 17 is diagram of exemplary frequency components of the asymmetric tri-phasic pulse waveform of FIG. 16.

FIG. 17 shows frequency components of the asymmetric tri-phasic pulse waveform 100 of FIG. 16. The frequency component profile 1702 includes the voltage magnitudes of the frequencies from 0-60 kHz that can be sensed when the asymmetric pulse waveform 100 is injected. From another point of view, the voltages from the collection of frequencies represented by the component profile 1702 are integrated by the sensed signal processor 606 to obtain an area value. This profile 1702 has some peaks and valleys that can provide useful spectroscopy in that differences from this profile 1702 in the sensed signal can indicate tissue changes or various patient conditions.

As shown in inset 1704, it should be noted that the exemplary asymmetric pulse waveform 100 provides no DC component, that is, the frequency component profile 1702 has no component at DC (i.e., 0 Hz). It is also significant that at the sensing range of 10-120 Hz for making electrograms, there is only a very tiny AC voltage component. The negligible AC voltage component in this sensing frequency range minimizes noise injection to electrogram sensing when the exemplary current waveform 100 is injected.

Figure 18:
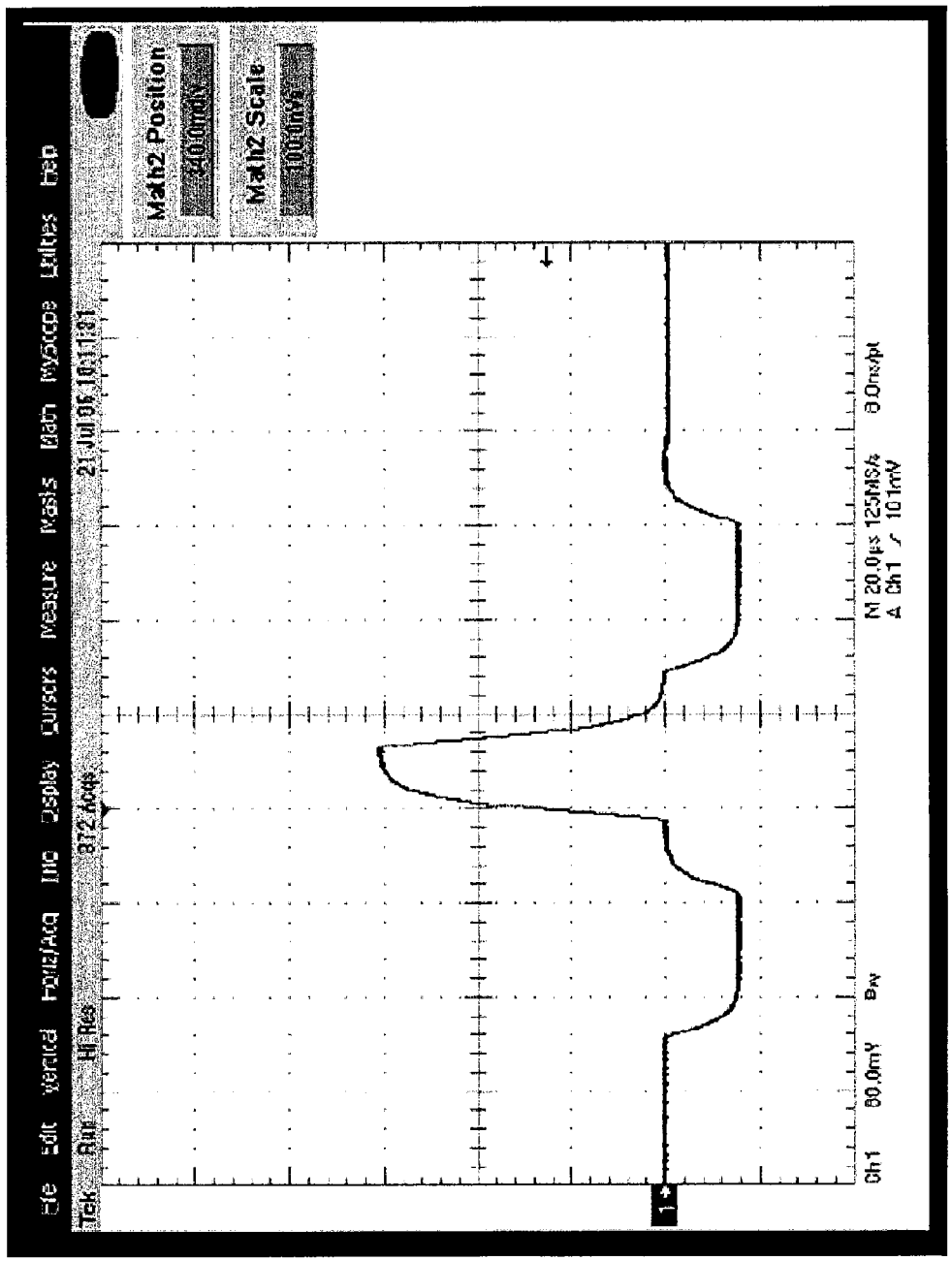
FIG. 18 is a screen shot of a sensed voltage waveform resulting from application in tissue of the exemplary asymmetric tri-phasic pulse waveform of FIG. 16.

FIG. 18 shows an example of a measured asymmetrical voltage pulse waveform 102 resulting from injection of the asymmetric current pulse waveform 100 of FIG. 16.

Figure 19:
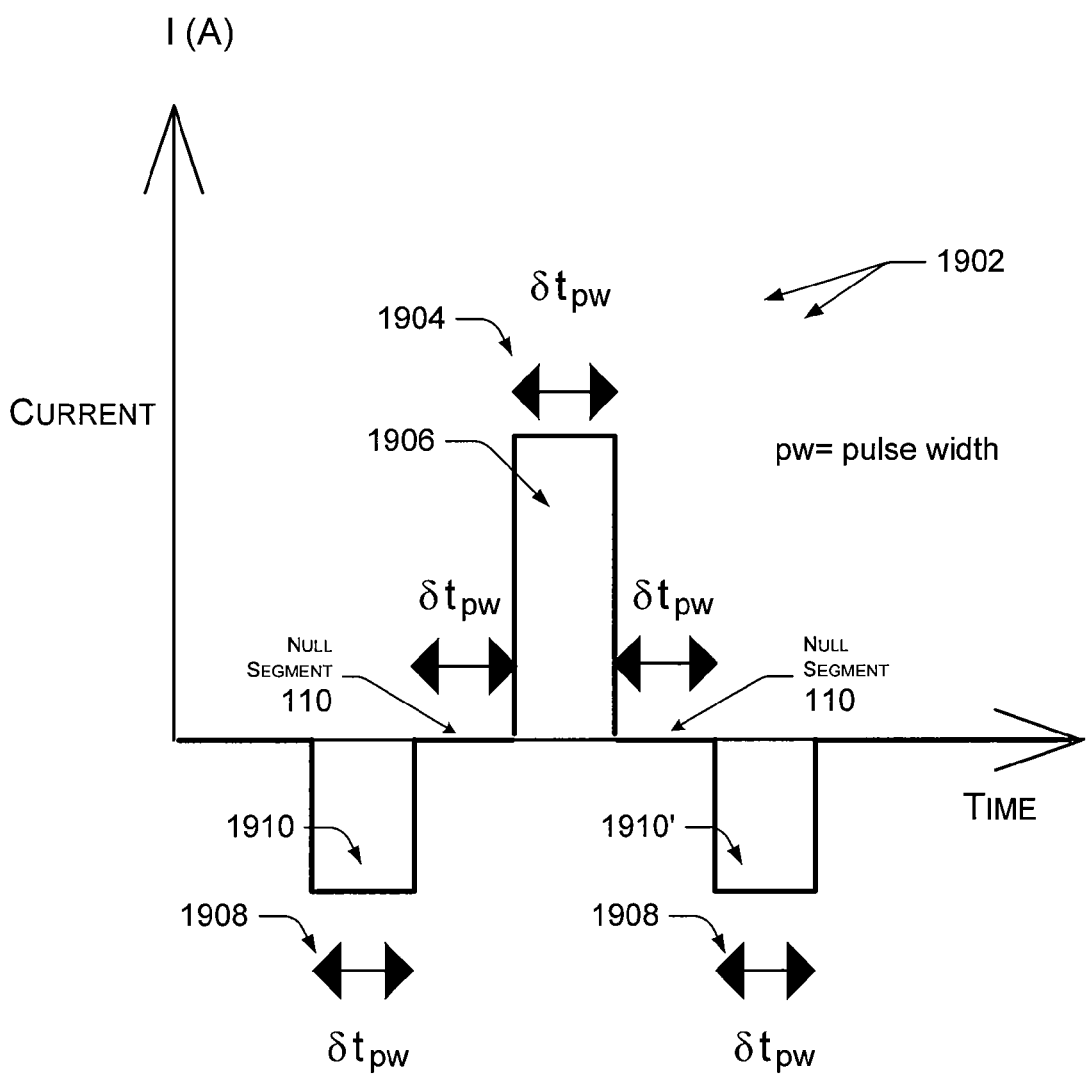
FIG. 19 is a diagram of an exemplary symmetric tri-phasic pulse waveform.

FIG. 19 shows an exemplary implementation of a symmetric pulse waveform 1902. The waveform shape is symmetrical because the width 1904 of the positive phase 1906 of the pulse waveform 1902 is equal to the width 1908 of the negative phase(s) 1910 of the pulse waveform 1902. Like the asymmetric pulse waveform 102, the symmetric pulse waveform 1902 has two negative phases 1910 that are designed to balance the positive phase 1906 of the pulse waveform 1902. This results in no DC component between the injection leads.

Figure 20:
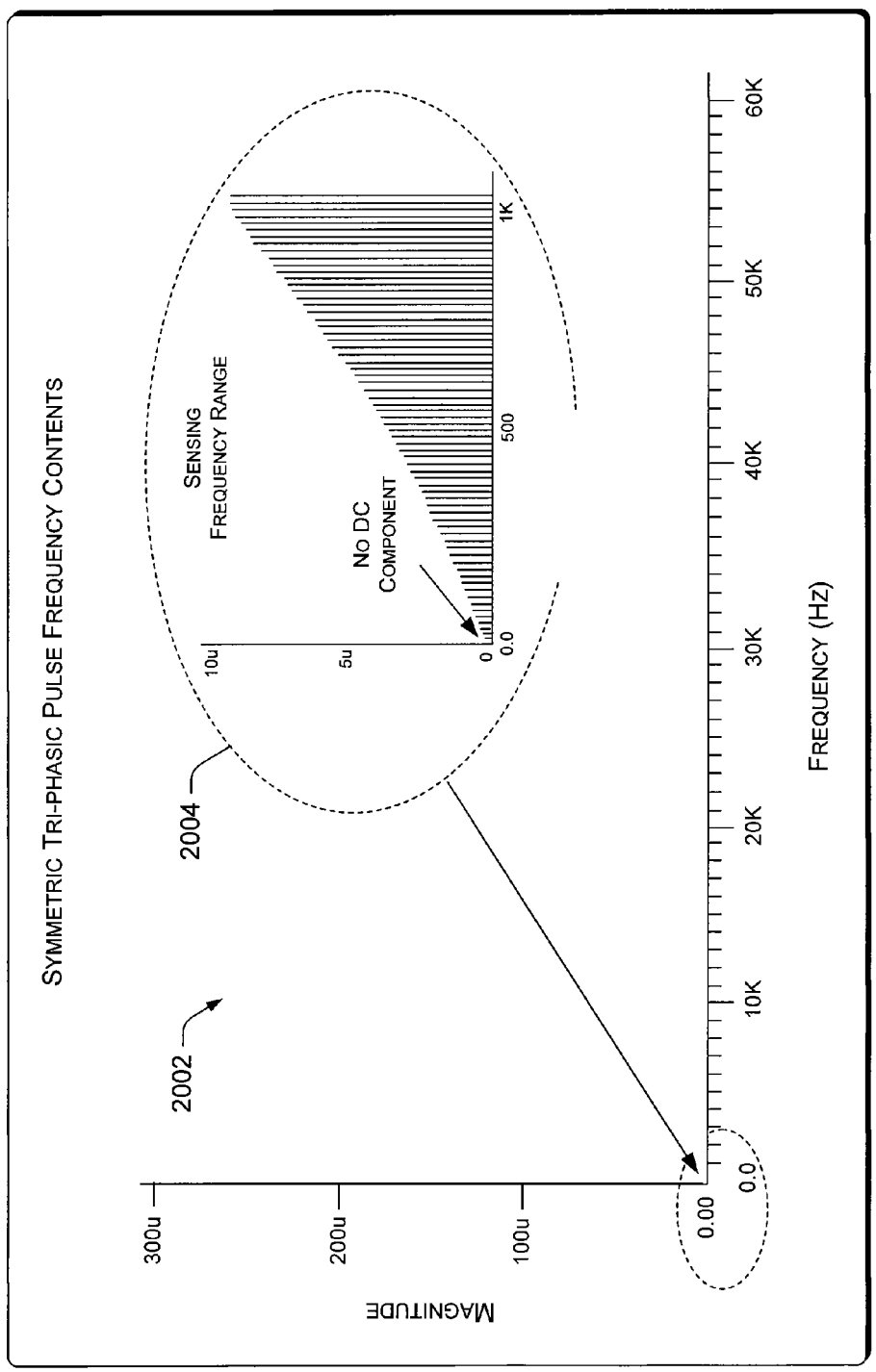
FIG. 20 is diagram of exemplary frequency components of the symmetric tri-phasic pulse waveform of FIG. 19.

FIG. 20 shows frequency components of the symmetric tri-phasic pulse waveform 1902 of FIG. 19. The frequency component profile 2002 includes the magnitudes of the frequencies from 0-60 kHz that can be sensed when the symmetric pulse waveform 1902 is injected. This profile 2002 has some peaks and valleys that can provide useful spectroscopy in that differences from this profile 2002 in the sensed signal can indicate tissue changes or various patient conditions. A close-up view 2004 shows an exemplary sensing frequency range of, for example, 10-120 Hz, in which there is only a tiny AC voltage component. It should be noted that the exemplary symmetric pulse waveform 1902 provides no DC component, and thus exemplary sensing frequency ranges do not include sensing a DC component of the sensed signal.

Figure 21:
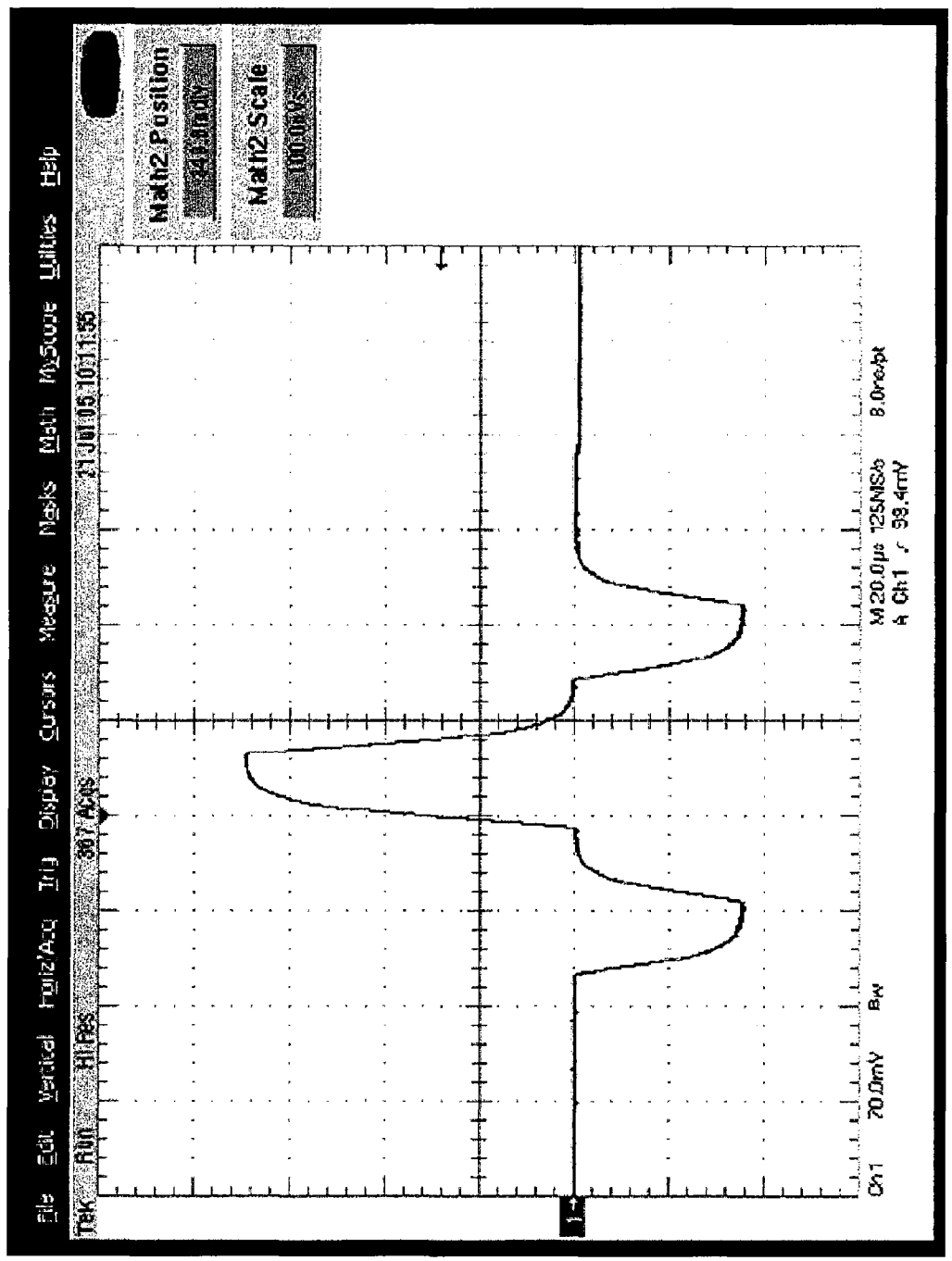
FIG. 21 is a screen shot of a sensed voltage waveform resulting from application in tissue of the exemplary symmetric tri-phasic pulse waveform of FIG. 19.

FIG. 21 shows an example of a measured symmetrical voltage pulse waveform 102 resulting from injection of the symmetric current pulse waveform 1902 of FIG. 19.

Figure 22:
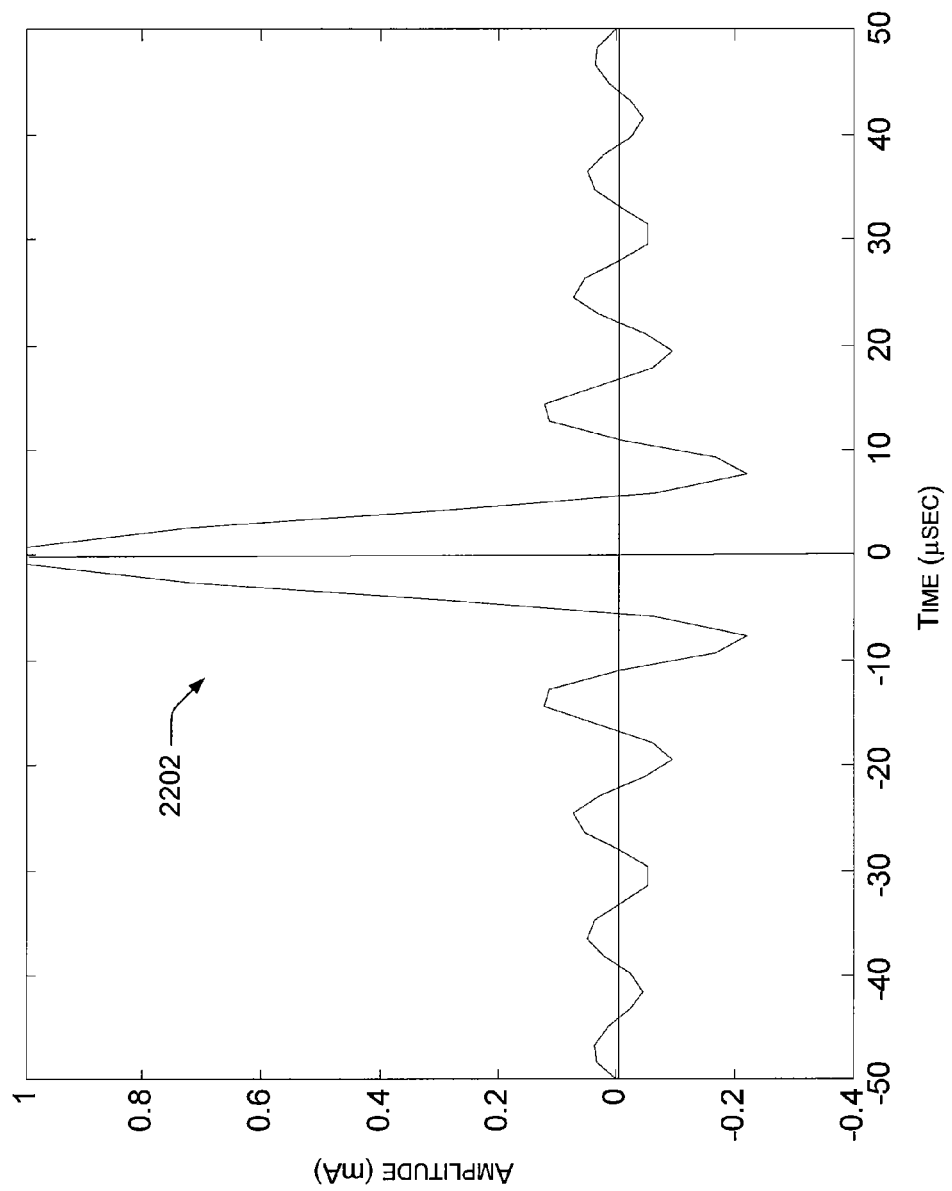
FIG. 22 is a diagram of an exemplary sinc multi-phasic waveform.

FIG. 22 shows an alternative waveform 2202 for either current or voltage injection. The waveform 2202 is generated by the sine cardinal function "sinc(x)," approximating the quantity sin(x)/x except in one implementation where at x=0 the sinc(x) function is assigned a value of 1. The sinc(x) waveform 2202 provides a wide and quasi-flat frequency spectrum. FIG. 22 shows the multiphase character of the sin(x)/x waveform 2202. This alternative waveform 2202 is shown with 17 phases, 9 positive phases and 8 negative phases, which balance each other to provide a charge-balanced and voltage-balanced waveform 2202.

The exemplary waveforms, e.g., 100 and 2202, provide many advantages over conventionally injected signals. Because of their short wavelength, low energy, and balanced charge and voltage between phases within a pulse, the exemplary waveforms 100 minimize intrusiveness. The exemplary waveforms 100 also avoid creating polarizations at electrode and measurement block interfaces, instead maintaining a neutral tissue environment that has not been violated or changed by their injection.

Figure 23:
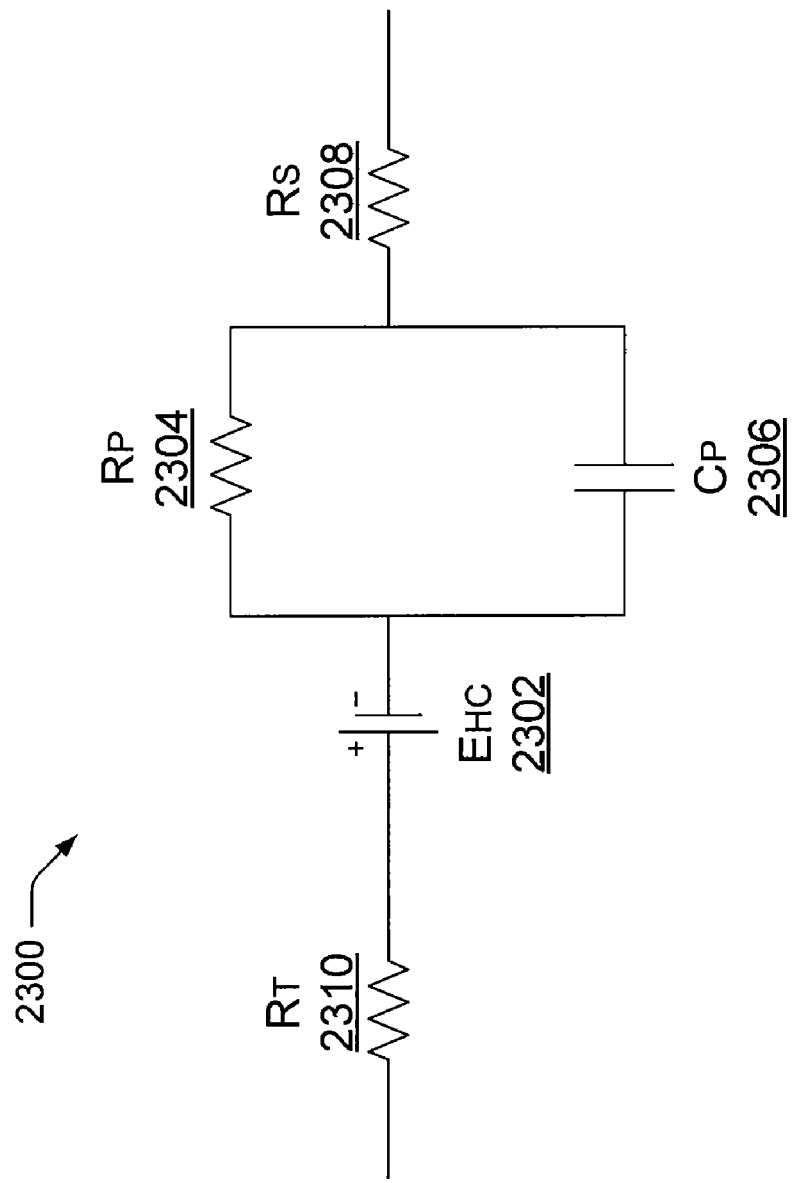
FIG. 23 is a block diagram of an exemplary electrical circuit modeling an electrode-to-tissue interface.

FIG. 23 shows an electric circuit diagram that models the electrochemical interface 2300 between an implanted electrode and adjacent tissue. The exemplary waveforms (e.g., 100) described above are injected into bodily tissue and also sensed via electrodes made of conduction materials, such as metals. $E_{hc}$ 2302 represents the half-cell voltage for a particular metal-electrolyte combination, $R_p$ 2304 and $C_p$ 2306 are the parallel resistor and capacitor, respectively, that model the interface. $R_s$ 2308 is the serial resistance of the electrode and $R_t$ 2310 is the tissue resistance.

Typical values found in the literature for $R_p$ 2304 and $C_p$ 2306 are in the range from 200-2000 ohms and 0.5 to 5.0 µF, respectively. Thus, the equivalent typical time constants can be in the range from 0.1 to 10.0 milliseconds. The exact values depend on size of the electrode, material and electrolyte type. Similarly, $E_{hc}$ can be as high as 0.7 volts.

Conventional tissue impedance circuits and methods typically intend to measure $R_t$ 2310. But it is desirable to minimize in particular the effects that $R_p$ 2304, $C_p$ 2306, and $E_{hc}$ 2302 may have on measurement accuracy. Such detrimental effects manifest in the form of long wait times required to allow the interface to settle, impedance errors introduced by $R_p/C_p$, offsets introduced by $E_{hc}$ 2302, etc. Injection of one of the exemplary waveforms (e.g., 100) has a better chance of achieving desired measurement goals. The duration of the waveform is shorter than conventional, or at least comparable to the time constants of the electrode-electrolyte interface. Consequently, the waveform 100, in its various implementations, has a decreased chance of disturbing the polarization potentials seen at the interface. Thus, artifacts introduced in the measurement process are minimized.

At the electrode-electrolyte interface of a typical lead, for example, the exemplary injected pulse waveforms 100 remain invisible, and do not allow polarization to build up at the interface. This is because the duration of the waveforms 100 is extremely short—e.g., 15 microseconds for the center pulse—as compared with conventional sensing waveforms that may have a 15 millisecond width per pulse (a duration that is about or over 1000 times greater than the exemplary waveform 100). Given the short width of the exemplary waveforms 100, the injected signal travels through all the illustrated capacitors in the model circuit thereby causing measurements to reflect the impedance of the tissue itself, unlike conventional techniques that inject signals that charge up capacitors $C_p$ 2306 and disturb the half-cell battery $E_{hc}$ 2302. ($E_{hc}$ 2302 is not like the common conception of a battery, but is formed by chemical reactions that can easily be disturbed.) The delicate ionic concentrations in the vicinity of the electrodes can easily be disrupted when current flows through the interface for too long of a time. For example, a conventional pulse width of 15 milliseconds is enough to get some ions or electrons that are being injected to disturb the chemical reactions of the interface 2300. On the other hand, because of the shortness of the exemplary pulse waveforms 100, the chemical reactions do not have a chance to be influenced by the injected exemplary pulse waveform 100, and net charge and voltage balances are zero.

Additional Data Acquired Via Exemplary Waveforms

The exemplary waveform, in its multiple implementations (e.g., waveform 100) can be used in several different ways to probe multiple physiological parameters, detect changes in hemodynamic functioning, detect changes in physical structure, and differentiate or characterize tissues.

As described above, the exemplary waveforms 100 do not have a DC component and the exemplary sensed signal processor 606 does not possess any circuitry with which to measure DC. Instead, injected exemplary waveforms 100 provide a rich spectrum of frequency content, and the frequency spectrum is quite broad, as shown in FIGS. 17 and 20. This property of the waveforms 100 is useful for many other types of tests and measurements. For example, the waveforms 100 can be used for tissue characterization and/or differentiation without adding hardware to create many frequencies via sweeping a signal through a frequency range.

The wide frequency spectrum characteristic of the exemplary waveforms 100 can be used to implement algorithms that differentiate tissues based on their frequency response to the injected waveform 100. For example, the characteristic impedance response to frequency variation in infarcted myocardium is relatively flat while the impedance of healthy myocardium is responsive to variations in frequency of an applied signal.

Figure 24:
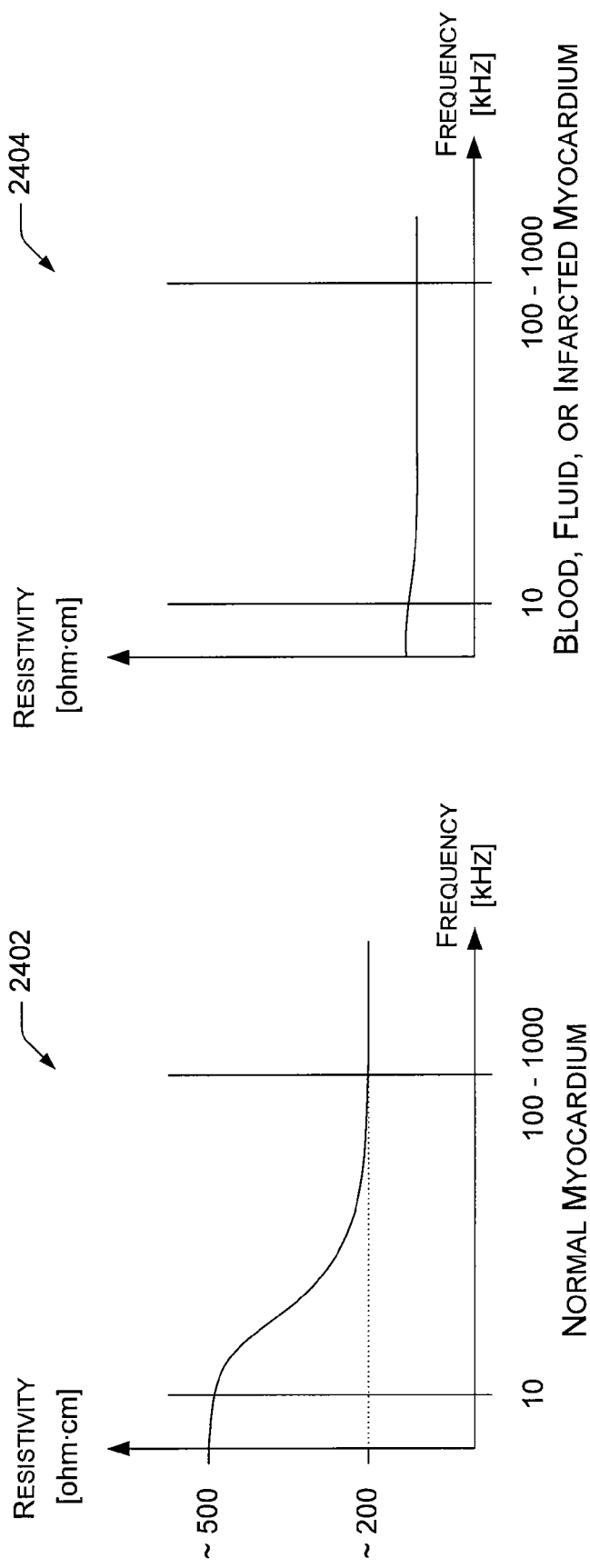
FIG. 24 depicts respective diagrams of the impedance response to frequency variations in normal myocardium and infarcted myocardium, when the exemplary waveforms of FIG. 1 are applied.

FIG. 24 shows characteristic tissue impedance frequency responses 2402 and 2404 that result when an exemplary waveform 100 impinges on reactive tissue (i.e., frequency responses 2402) and on non-reactive tissue (i.e., frequency responses 2404), respectively. Reactive tissue is almost always healthy tissue, in which impedance varies in relation to the applied frequency of the injected signal due to the capacitive character of living cell membranes. Whereas resistors allow a flow of electrons through them directly proportional to the voltage drop, capacitors oppose changes in voltage by drawing or supplying current as they charge or discharge to the new voltage level. The flow of electrons "through" the capacitance of a healthy tissue is directly proportional to the rate of change of voltage across the tissue. Thus, if the width of the applied current signal is relatively short, the signal has higher frequency and will pass more easily through capacitance of healthy tissue (healthy tissue passes relatively high frequencies more readily than lower frequencies).

Blood is sometimes considered a tissue, and is an exception to this phenomenon. The impedance of infarcted tissue, blood, lymph, edema fluids, etc., typically does not vary significantly in relation to the applied frequency of an injected signal. So, if a spectrum of frequencies are applied to tissue and thus made available for an implantable device to sense, then fluid, blood or infarcted tissue, etc., can be discriminated from healthy tissue because the fluid, blood or infarcted tissue has a flatter frequency response, i.e., impedance does not vary much when the frequency of applied signals changes. The exemplary waveforms 100 provide a frequency-rich signal for distinguishing between types of tissue in this manner. Not only can the waveforms 100 be used to differentiate tissue, but also in an exemplary multi-vector network this property can be used to actually locate unhealthy (e.g., infarcted) areas of tissue.

The voltage pulse waveform 102 sensed from healthy or otherwise reactive tissue has been affected by the capacitive reactance of the responsive tissue, as shown in the characteristic impedance frequency response 2402. Since the reactive tissue has some capacitive character, its resistivity increases at low frequencies—i.e., healthy tissue has a tendency to block low frequencies and pass high frequencies as a capacitor would. The resistivity then decreases and levels off as the frequency of the injected signal increases, thus the impedance frequency response 2402 is somewhat "S" shaped.

Infarcted tissue, blood, edematous fluids, etc., on the other hand, tend to behave more like a pure resistor to AC current, and thus the capacitive effect is reduced as shown in the characteristic frequency response 2404. The resistivity tends to remain about the same through the frequency spectrum, blood having a fairly constant resistivity of approximately 150 ohm-centimeters, and infarcted tissue having a fairly constant resistivity in the range of several hundred ohm-centimeters. The impedance of blood is vastly independent of applied frequency, that is, approximately the same impedance value is measured whether the applied frequency is 100 Hz or 100 kHz. This characteristic is similar for infarcted tissue.

Consequently, when the impedance measurement is flat over a spectrum of applied frequencies, then the exemplary implantable device 200 concludes that the tissue around the sensing electrode or within the vector being measured is infarcted in a higher percentage or congested with blood or other bodily fluid, as if when assessing pulmonary edema. But if this impedance measurement varies according to sensed frequency, then the implantable device 200 can conclude that the vast majority of tissue around the sensing electrode or within the vector being measured is healthy tissue. As introduced above, when the exemplary waveform 100 is used, the electronics of the implantable device 200 do not have to sweep a range of frequencies via the injected signal, requiring modification and/or special hardware. Rather, because the exemplary injected waveform already provides the wide frequency range within itself, little or no hardware modification is needed.

Besides using characteristic impedance frequency responses 2402 and 2404 to differentiate types of tissue (and thereby sense conditions such a cardiac enlargement—such as in congestive heart failure conditions, infarcted tissue, pulmonary edema, etc.) the exemplary waveforms 100 can be used in other ways to differentiate tissues. In one exemplary technique, an implantable device 200 can differentiate tissues by modulating a dimension of an exemplary waveform 100 being injected, and then sensing the tissue response. In another exemplary technique, an implantable device can differentiate tissues by sensing differences in a phase delay introduced between injected signal and sensed signal due to the type of tissue providing the electrical path. These techniques will now be described.

Modulating one or more aspects of the geometry of the exemplary pulse waveform 100 can sometimes create a tool that is probative of a tissue parameter. For any given magnitude of AC voltage at a given frequency, the capacitance of a given vector of healthy tissue will "conduct" a certain magnitude of AC current. Just as the current through a resistor is a function of the voltage across the resistor and the resistance offered by the resistor, the AC current through a capacitor is a function of the AC voltage across it, and the reactance offered by the capacitor.

Since capacitors "conduct" current in proportion to the rate of voltage change, they will pass more current for faster-changing voltages (as they charge and discharge to the same voltage peaks in less time), and less current for slower-changing voltages. What this means is that reactance in ohms for any capacitor (or tissue) is inversely proportional to the frequency of the alternating current.

Thus, in one implementation shown in FIG. 25, the width (or duration) of the waveform 100 is modulated to gauge how the intervening tissue reacts. For example, the applied waveform 100 can be varied continuously from a first width 2502 to a second width 2504 or alternatively, only a first width 2502 and a second width 2504 are discretely applied as pulses to the tissue. If the duration of the pulses is varied by changing the duration of one or more positive phases of the waveform, then negative phases of the waveform are adjusted to maintain a current-balanced and voltage-balanced waveform. Since fluids, blood, and infarcted tissue behave more like a pure resistor and without significant capacitive character compared with healthy tissue, the shape of the resulting sensed waveform does not vary much when the duration of the pulses are modulated. Thus, when there is a relatively high percentage of fluid, blood, or infarcted tissue present, the waveform shape represented in the sensed signal does not vary much, and tends to mirror the waveform shape (2506, 2508) of the injected signals 2502 or 2504 with their respective differences in pulse width.

In FIG. 26, the capacitive content of healthy tissue affects the shape of the resulting sensed voltage. For a longer injected current duration, as in waveform 2604, the capacitance found in healthy tissue is allowed to charge for a longer time. Consequently, the shape of the sensed voltage 2608 displays a longer ramp (a sign of capacitive charging) than that of sensed voltage 2606 (that corresponds to an injected current of shorter duration, 2602). Thus, when tissue behaves with capacitive character in this manner, the initial voltage $V_0$ is less than a peak voltage $V_P$ at the end of the current pulse.

If the applied current pulse positive phase 106 is modulated in succeeding pulses from a first width 2602 to a second width 2604, then the voltage of the sensed voltage waveform 102 may correspondingly continue to increase until a second peak voltage $V_{P'}$ is reached at the end of the of the sensed voltage waveform 102 now having a second width 2608. As a technique for differentiating infarcted tissue, etc., from healthy tissue, the morphology 2610 of the sensed voltage waveform 102 for healthy tissue is distinct from the voltage waveform 102 for non-reactive tissues in FIG. 25. It is relatively easy for an implantable device 200 to modulate the width 2502 of applied pulse waveforms 100 in order to make this differentiation, e.g., between infarcted tissue and healthy tissue. In some circumstances, this technique may be easier to implement than sensing a relative continuum of frequency responses (e.g., as in FIG. 24).

In FIG. 25, the ratio $V_P/V_0$ remains approximately equal to 1 if the tissue being sensed is mostly infarcted tissue, blood, edematous fluid, etc., as in Equation (1):

$$\frac{V_P}{V_0} \cong 1 \tag{1}$$

If the ratio $V_P/V_0$ remains less than the ratio $V_{P'}/V_0$ as the width of the injected pulse is increased, however, then the tissue being sensed is mostly healthy tissue, as in Equation (2):

$$\frac{V_P}{V_0} < \frac{V_{P'}}{V_0} \tag{2}$$

Since tissue along any given vector may be a mixture of healthy tissue and infarcted tissue (e.g., an infarcted area in an otherwise healthy heart) an exemplary implantable device 200 may determine a ratio of infarcted tissue to healthy tissue. This ratio may then be reported to a practitioner or fed to a treatment algorithm onboard the implantable device 200. Likewise, the same type of ratio may measure a blood, or bodily fluid, to tissue ratio. Changes in this ratio may indicate that the heart is enlarging along a certain vector, i.e., a greater blood to healthy tissue ratio along a vector that includes the left atrium would indicate enlargement of this heart chamber, as it would happen in patients suffering of heart failure. Alternatively, this ratio may indicate blood or bodily fluid accumulation in the lungs, as the case would be for patients experiencing pulmonary edema, if the measurement vector includes lung tissue in its electrical path. Of course, the specificity of these ratios can be increased when performed on multiple vectors of the multi-vector network at once. The differences in the ratios between vectors can triangulate to an ischemic or infarcted lesion, for example.

Figure 27:
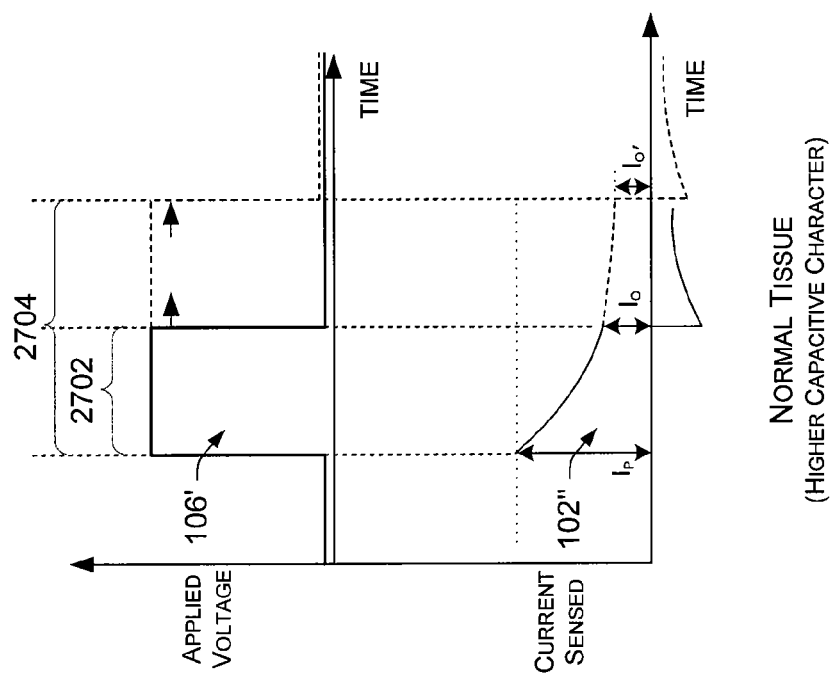
FIG. 27 is a diagram of an exemplary waveform shape response of normal tissue to modulated width of applied voltage pulse waveforms.

FIG. 27 shows another implementation of the exemplary technique shown in FIGS. 25 and 26 as applied to normal tissue (that possesses some capacitive character). In FIG. 27, an exemplary implantable device 200 injects a voltage pulse 106' instead of a current pulse. Then, a current waveform 102" is sensed instead of voltage, e.g., by an alternative version of the sensed signal processor 606.

If an implantable device lengthens the width of the applied voltage waveform, then the signal has a lower frequency component and the capacitance of healthy tissue has more of a tendency to block this lower frequency. So, by modulating width of the applied voltage waveform to a longer wavelength, the morphology of the resulting current signal changes, as illustrated. This exemplary "frequency scan" from one applied voltage pulse wavelength width to a longer one is easy to implement in an implantable device (without changing hardware much—the device just applies a short width then a long width, and then analyzes the resulting current signal).

Thus, in FIG. 27 the peak current $I_P$ occurs at the outset of the sensed current waveform 102" when the change in the applied voltage is very great, as the capacitor formed by the tissue "charges" to the new voltage level. By the end of the applied voltage pulse 106', the lagging current has decreased to a value $I_0$ at the end of the applied voltage pulse 106'. If the width of the applied voltage pulse 106' is expanded from width 2702 to width 2704, then the current waveform 102" decreases further to a value $I_{0'}$.

This sensed current waveform morphology of FIG. 27 can be used to distinguish normal reactive tissue from infarcted tissue, blood, fluid, etc., as the latter would display a sensed current waveform in which the sensed waveform mirrors the applied voltage waveform, since infarcted tissue, blood, fluid, etc., behave more like a pure resistor.

In FIG. 27, the ratio $I_P/I_0$ remains approximately equal to 1 if the tissue being sensed is mostly infarcted tissue, blood, edematous fluid, etc., as in Equation (3):

$$\frac{I_P}{I_0} \cong 1 \tag{3}$$

If the ratio $I_P/I_0$ remains less than the ratio $I_P/I_{0'}$ as the width of the injected pulse is increased, however, then the tissue being sensed is mostly healthy tissue, as in Equation (4):

$$\frac{I_P}{I_0} < \frac{I_P}{I_{0'}} \tag{4}$$

Ratios such as "blood to tissue" or "infarcted tissue to normal tissue" may be determined by an implantable device 200 that injects voltage and senses current in a similar manner as described above for implementations that inject current and sense voltage.

Figure 28:
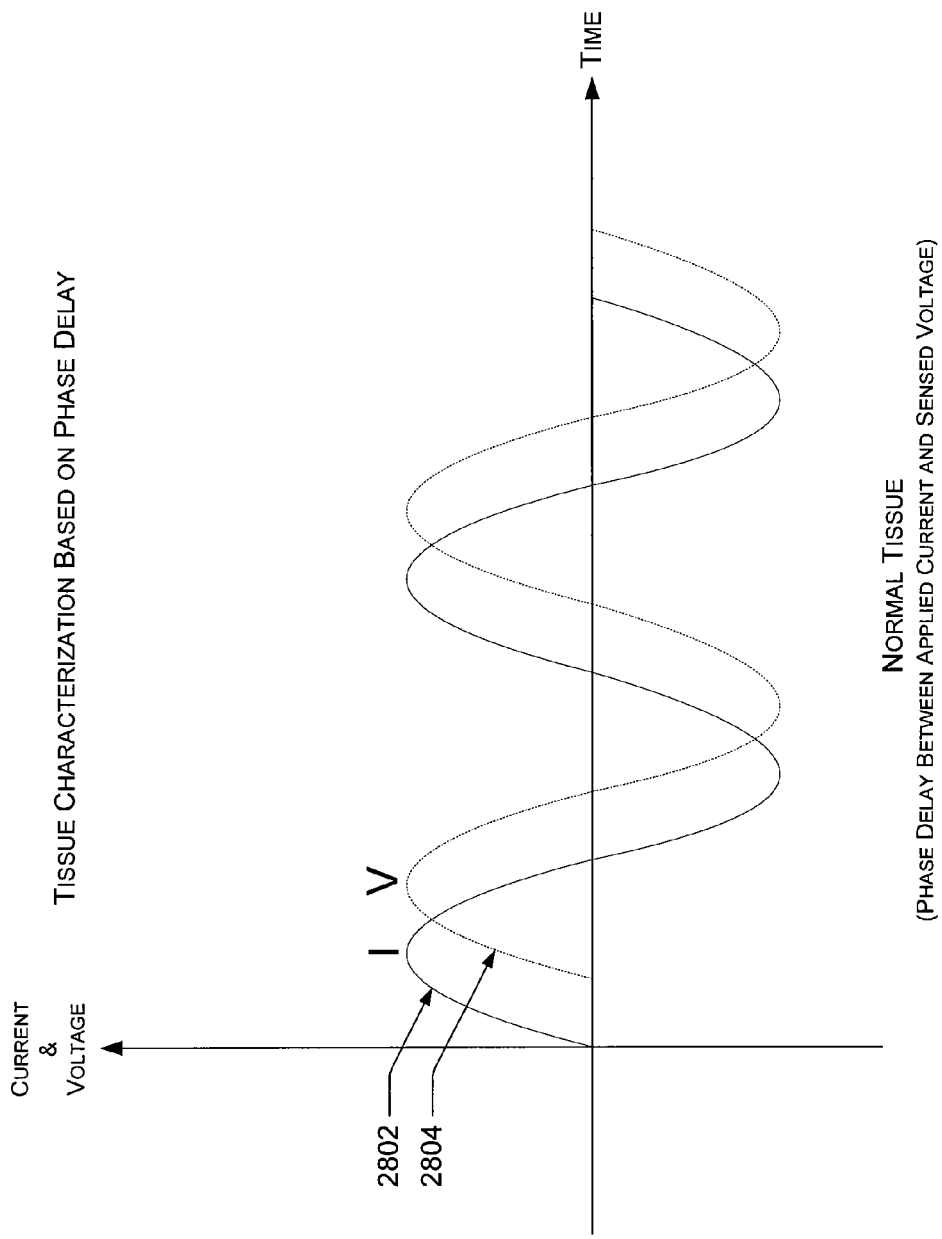
FIG. 28 is a diagram of exemplary tissue characterization based on sensed phase delay between applied and sensed exemplary waveforms.

With a pure resistor the injected current and measured voltage are in phase. Resistive tissues like infarcted tissue, bodily fluids, blood, etc., introduce little phase delay. The current through the capacitance of healthy tissue, on the other hand, is a reaction against the change in voltage across it. Therefore, more phase delay between the voltage and current signals can be measured in normal or healthy tissues. As illustrated in FIG. 28, the current wave 2802 has a head start on the voltage wave 2804; the current leads the voltage, and the voltage lags behind the current. Healthy tissue is not really a pure capacitor, of course, but has more capacitance than infarcted tissue or blood, for example.

It is relatively easy for an implantable device 200 to detect the phase angle between an injected current waveform 100 and a sensed voltage waveform 102, as the phase delay manifests itself as a temporal delay between peaks (e.g., in sinusoidal versions of the exemplary waveform (2202 in FIG. 22)) or a temporal delay between corresponding parts of the applied and sensed waveforms (e.g., a time delay between leading edges). In one implementation, the phase delay does not affect measuring overall areas of the applied current waveform and the sensed voltage waveform since this implementation does not try to measure at particular pre-specified points in corresponding waveforms as is conventionally performed. Instead, exemplary integration of areas are just shifted in time from each other, since voltage is shifted with respect to current.

Diagnostically, then, a decreased phase delay between injected waveform and sensed waveform is expected if the tissue surrounding the electrodes is affected by infarct. Similarly, fluids that may build up in the lungs (as happens in congestive heart failure patients) have a flat frequency characteristic. Consequently, a diminishing phase delay is expected between sensed and injected signals as fluid accumulates in the lungs. Some implementations of the sensed signal processor 606 have the capability to acquire and measure such phase delays, in addition to calculating impedance.

Exemplary Methods

Figure 29:
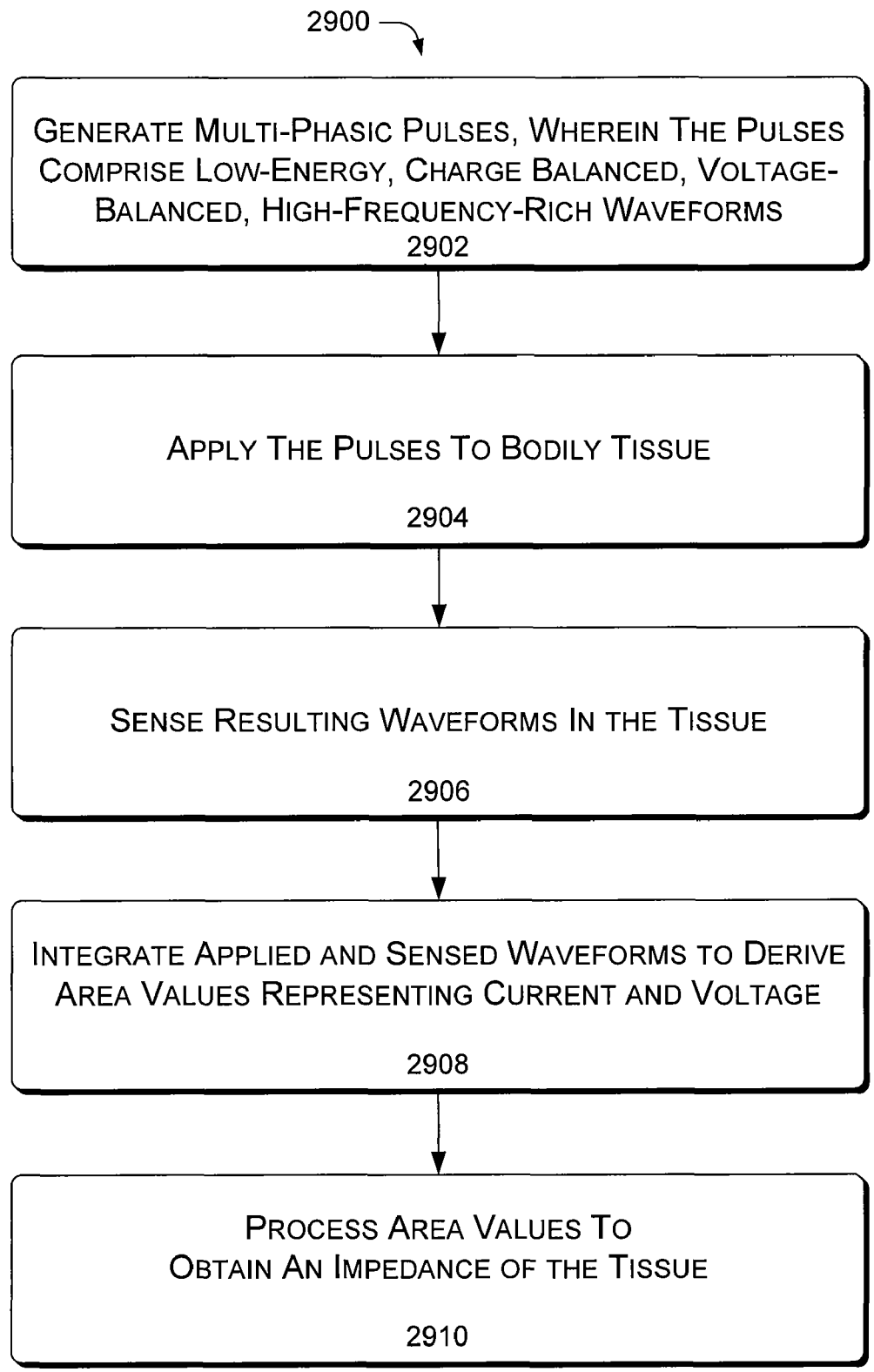
FIG. 29 is a flow diagram of an exemplary method of obtaining an impedance value of tissue.

FIG. 29 shows an exemplary method 2900 of obtaining an impedance value of bodily tissue. The exemplary method 2900 may be implemented in connection with many suitably configured stimulation devices, although it will be described as being executed by the exemplary impedance measurement circuit architecture 600 of the exemplary implantable device 200. In the flow diagram of FIG. 29, the operations are summarized in individual blocks. Some operations may be performed in hardware and/or as machine-readable instructions (software or firmware) that can be executed by a processor, such as microcontroller 421.

At block 2902, pulses are generated by an implantable device. Pulses may be either current pulses or voltage pulses. Each pulse has a multi-phasic waveform consisting of n positive phases and n+1 negative phases. The negative and positive phases alternate. Typical variations are a tri-phasic waveform, a 5-phase waveform, and a sinusoidal implementation approximating $\sin(x)/x$ (or $\text{sinc}(x)$). Null segments can be implemented between the negative and positive phases of a waveform in order to facilitate the processing conducted by the hardware.

Each pulse conforming to the exemplary waveform is of low energy, compared with conventional pulses used to probe impedance. For example, each positive phase may be only 1 milliamp. The negative phases of a multi-phasic waveform do not have as great an amplitude as the positive phase(s). However, all the negative phases and all the positive phase(s) of a single pulse waveform add up to provide not only a net-zero charge but also a net-zero voltage.

These exemplary waveforms are rich in high frequency content, especially square wave versions. Both symmetric and non-symmetric variations are available. A symmetric variation of the waveform has negative phases with the same duration as the positive phases, e.g., a tri-phasic waveform with one positive phase preceded and followed by a negative phase, all three phases having a duration of 15 microseconds each. In such an implementation, the amplitudes of the two negative phases are such that they balance the positive phase. An asymmetric version of the waveform has a positive phase of, for example, 15 microseconds, and negative phases of, for example, 30 microseconds apiece. If the amplitude of the positive phase is, for example, 1 milliamp, then the amplitude of each negative phase is 0.25 milliamps to balance the positive phase. Such a low energy and short duration pulse efficiently probes tissue without building up charge or voltage excesses, without polarizing interfaces, and is generally imperceptible to a patient.

At block 2904, the pulses are applied to a bodily tissue. The application can be made via two or more electrodes or electrode configurations of an implanted lead system. Ideally, the pulses are applied over several vectors of a multi-vector network to create a network of values. This network of values not only increases reliability, but also increases the specificity and sensitivity of the implantable device to the parameter being measured. However, single-vector networks can be used as efficiently.

At block 2906, the resulting waveforms are sensed. That is, the applied or injected pulse waveforms are affected by the tissue in the electrical pathway of the selected application vector and the resulting electrical effects may then be sensed or detected. That is, the tissue itself becomes part of an electrical circuit, behaving like various circuit components or combinations of components, with electrical characteristics such as resistance, capacitance, resistance and capacitance in series, etc. Thus, a signal sensed from the tissue by the same or different electrodes may also possess waveform features that are understandable in terms of the waveform features of the applied pulses plus the tissue's effect on these applied waveforms.

At block 2908, in one implementation, the sensed waveforms are integrated to obtain an area value of the sensed waveform, i.e., the absolute value of each phase of the sensed waveform is evaluated for its area, and the areas of the multiple phases are summed.

At block 2910, an impedance value for the tissue path is obtained by comparing the calculated area of the sensed waveform with the corresponding area of the applied or injected waveform. For example, if the injected waveform is current, then the impedance value is obtained by dividing the voltage area by the current area. The area of the injected waveform is usually known or easily obtained, since an implantable device already knows the number and the morphology of the pulses it generates. Moreover, in many implementations the exemplary multi-phasic pulse waveforms have square wave phases making the area calculation easy. The impedance value obtained is reliable, because the exemplary waveform injected aims to not change the electrical properties of the tissue or the electrode tissue interface as conventional electrical pulses do. The technique of integrating the waveforms and comparing areas is also much more reliable than trying to sample the current or voltage at points in time that are contrived to coincide synchronously with the applied pulses. This latter conventional approach usually presents implementation inaccuracies, because the effects of phase delay, cardiac cycle, and respiratory cycle would have to be know beforehand for optimal synchronization, yet these effects are components of the parameter being measured.

Figure 30:
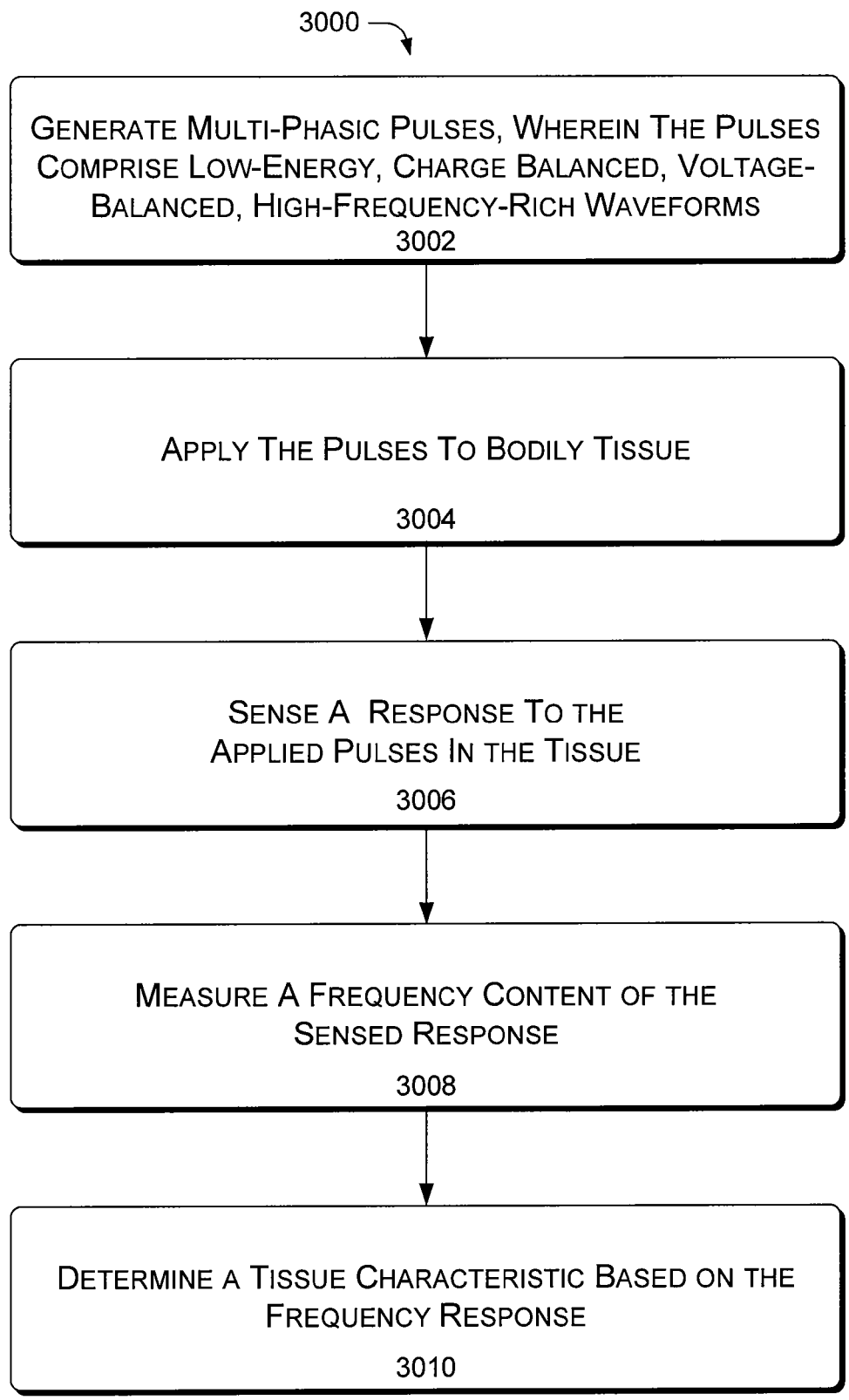
FIG. 30 is a flow diagram of an exemplary method of determining a tissue characteristic based on impedance response to frequency variations.

FIG. 30 shows an exemplary method 3000 of obtaining a tissue characteristic based on the frequency response of the tissue. The exemplary method 3000 may be implemented in connection with many suitably configured stimulation devices, although it will be described as being executed by the exemplary impedance measurement circuit architecture 600 of the exemplary implantable device 200. In the flow diagram of FIG. 30, the operations are summarized in individual blocks. Some operations may be performed in hardware and/or as machine-readable instructions (software or firmware) that can be executed by a processor, such as microcontroller 421.

At block 3002, exemplary pulse waveforms are generated as described for block 2902 of FIG. 29.

At block 3004, the pulse waveforms are applied to bodily tissue as described for block 2904 of FIG. 29.

At block 3006, a response is sensed to the applied pulses in the bodily tissue. In one implementation, if the applied pulses are current then the sensed response is voltage.

At block 3008, a frequency response of the tissue is measured, using the applied pulse waveforms. There is a characteristic impedance response to variations in frequency when exemplary waveforms are injected into healthy tissue that has substantial capacitance, and also a different characteristic frequency response when the waveforms are injected into infarcted tissue, blood, edematous fluid, etc., that lack significant capacitive character. For normal healthy tissue, the impedance typically varies in relation to the applied frequency of the injected signal due to the capacitive reactance of living cell membranes. But infarcted tissue, etc., behaves more like a pure resistor. Hence, the characteristic frequency response vis-à-vis impedance of infarcted tissue, etc., is relatively flat compared with healthy tissue.

At block 3010, a tissue characteristic is determined based on the frequency response. That is, in the measured frequency response, the relative similarity of the impedance readings to one type of characteristic frequency response or the other can be used to determine a percentage infarcted character, a blood to tissue ratio, a degree of edema, etc.

Figure 31:
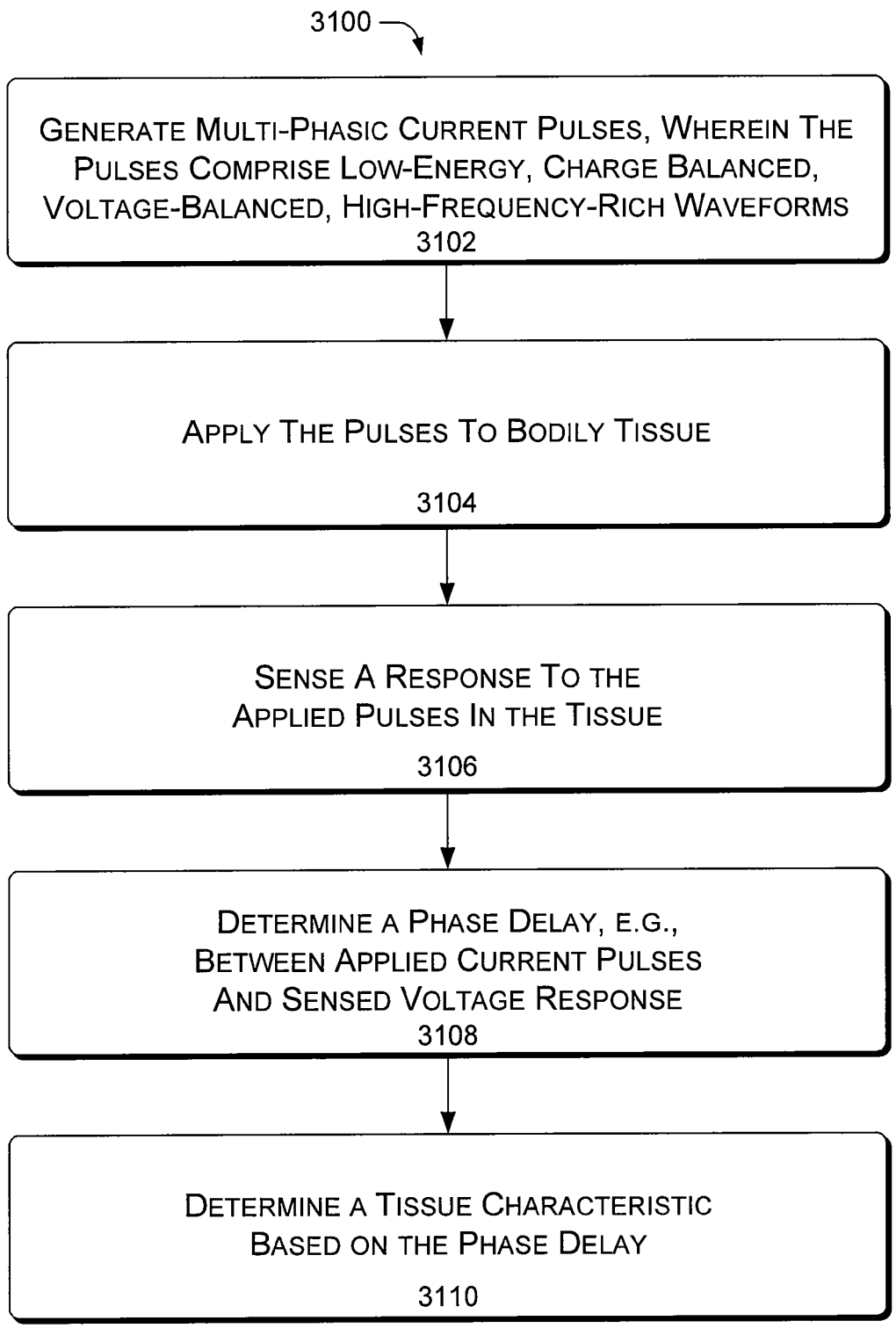
FIG. 31 is a flow diagram of an exemplary method of determining a tissue characteristic based on phase delay.

FIG. 31 shows an exemplary method 3100 of obtaining a tissue characteristic based on a phase delay between applied and sensed signals. The exemplary method 3100 may be implemented in connection with many suitably configured stimulation devices, although it will be described as being executed by the exemplary impedance measurement circuit architecture 600 of the exemplary implantable device 200. In the flow diagram of FIG. 31, the operations are summarized in individual blocks. Some operations may be performed in hardware and/or as machine-readable instructions (software or firmware) that can be executed by a processor, such as microcontroller 421.

At blocks 3102 and 3104, exemplary pulse waveforms are generated and applied to tissue as described for blocks 2902 and 2904 of FIG. 29.

At block 3106, a response to the applied pulses is sensed in the tissue. If the applied waveforms in one implementation are current pulses, then the resulting signal that is sensed is a voltage waveform. That is, a signal sensed from the tissue by one or more electrodes of a single- or multi-vector network also possess waveform features that are understandable in terms of the waveform features of the applied pulses plus the tissue's effect on these applied waveforms.

At block 3108, a phase delay between the applied current pulse waveforms and the sensed voltage response is determined. The degree of the phase delay is related to the capacitance of the tissue path, healthy tissue having a relatively high capacitance, and infarcted tissue, blood, edematous fluid, etc., having a relatively low capacitance.

At block 3110, a tissue characteristic is determined, based on the phase delay. That is, the degree of phase delay may be used to determine a characteristic of the tissue path, such as percentage of infarcted character, blood to tissue ratio, degree of edema, etc.

Figure 32:
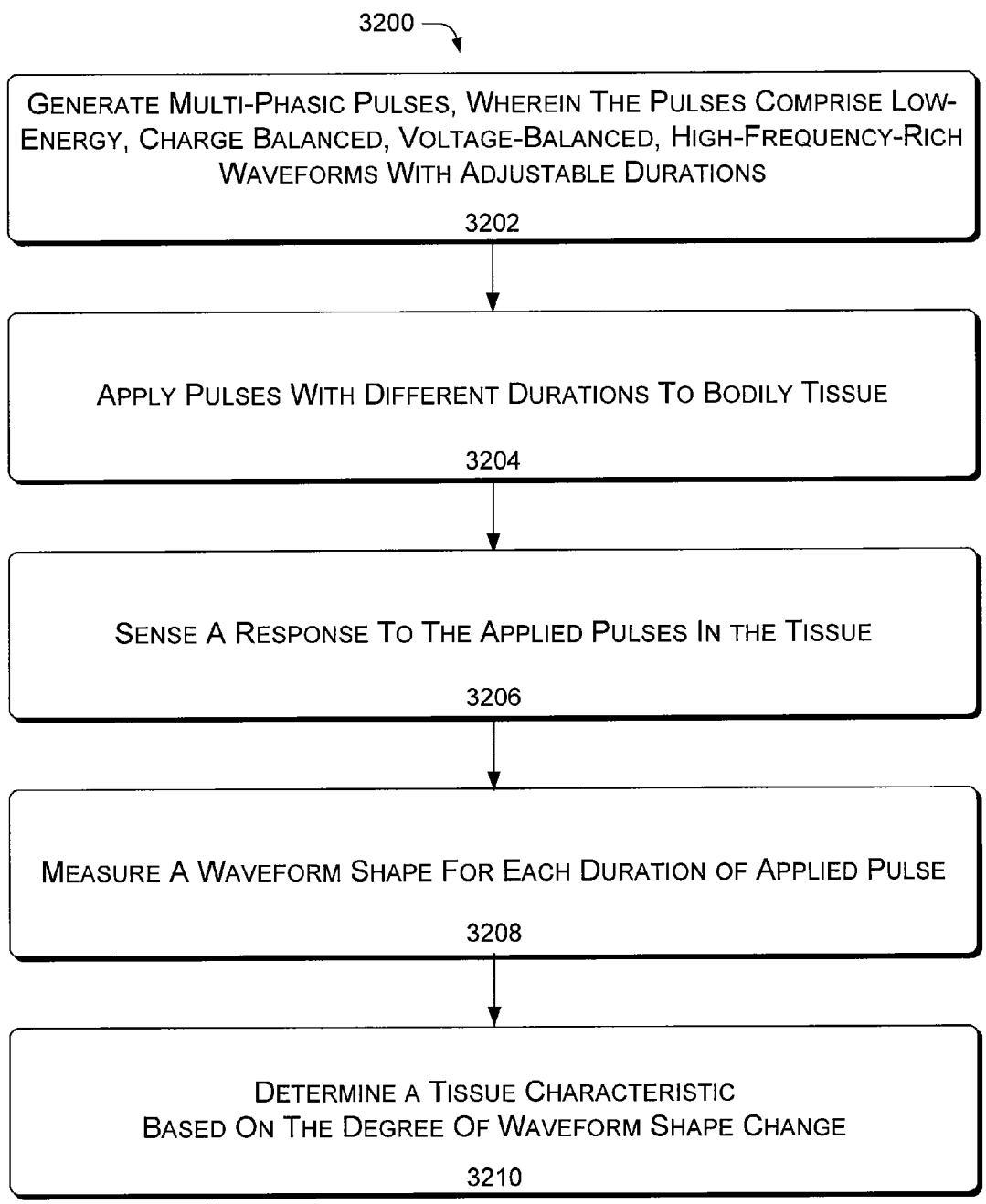
FIG. 32 is a flow diagram of an exemplary method of determining a tissue characteristic based on waveform shape response.

FIG. 32 shows an exemplary method 3200 of obtaining a tissue characteristic based on a waveform shape response to modulated pulse width. The exemplary method 3200 may be implemented in connection with many suitably configured stimulation devices, although it will be described as being executed by the exemplary impedance measurement circuit architecture 600 of the exemplary implantable device 200. In the flow diagram of FIG. 32, the operations are summarized in individual blocks. Some operations may be performed in hardware and/or as machine-readable instructions (software or firmware) that can be executed by a processor, such as microcontroller 421.

At blocks 3202 and 3204, exemplary pulse waveforms are generated and applied to tissue as described for blocks 2902 and 2904 of FIG. 29, with the addition that the exemplary waveforms are adjustable in their width (i.e., their duration). Thus, an exemplary device modulates the pulse width of the waveform, either continuously over a spectrum of widths, or by selecting a limited number of discrete widths, for example, two different durations of a tri-phasic waveform.

At block 3206, a response to the applied pulses is sensed in the tissue, i.e., resulting waveforms are sensed. A signal sensed in the tissue by the same or different electrodes possesses waveform features that are understandable in terms of the applied pulses and the intervening tissue. The sensed waveform response may vary as the duration of the applied pulses is varied for some types of tissues or conditions, while the sensed waveform response does not vary much as the duration of the applied pulses is varied for other types of tissues or conditions.

At block 3208, a waveform shape is measured for each duration of applied pulse. For example, in one implementation, if the tissue is mainly healthy, a longer injected pulse duration results in a sensed waveform response that displays a longer ramp (a sign of capacitive charging) than that of a sensed waveform response resulting from an injected pulse of shorter duration. Tissue that contains a high percentage of infarcted tissue, blood, fluid, etc., does not show this effect.

At block 3210, a tissue characteristic is determined based on the degree of waveform shape change as the duration of the applied pulses is varied. That is, the estimated degree of capacitance of the tissue path can be determined by the amount of morphology change as the applied pulse duration is varied. A low degree of capacitance is indicative of a relatively high percentage infarcted character, a relatively high blood to tissue ratio, a relatively high degree of edema, etc.

CONCLUSION

Although exemplary systems and methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method, comprising:
generating pulses in an implantable device, wherein a multi-phasic waveform of each pulse possesses alternating positive and negative phases, wherein each phase comprises a duration and an amplitude, wherein duration is defined as the width of the phase and amplitude is defined as the length of the phase, wherein the alternating positive and negative phases have an additive net-zero charge, wherein at least one negative phase has an absolute amplitude less than an absolute amplitude of one of the positive phases, and wherein the pulses are configured to generate a voltage on one or more capacitors of the bodily tissue and/or the implantable device in series with the impedance load of the bodily tissue path that has a zero-volt mean value;
applying the pulses to a bodily tissue;
measuring a frequency response of the bodily tissue to the applied pulses; and
determining a tissue characteristic based on the frequency response.

2. The method as recited in claim 1, wherein the tissue characteristic comprises a presence of infarcted tissue having a substantially flat frequency response over a spectrum of frequencies provided by the pulses.

3. The method as recited in claim 1, wherein the tissue characteristic comprises a blood to tissue ratio, wherein the blood has a relatively flat frequency response and the tissue has a capacitive frequency response over a spectrum of frequencies provided by the pulses.

4. The method as recited in claim 3, wherein the blood to tissue ratio indicates enlargement of a chamber of a patient's heart.

5. The method as recited in claim 1, wherein the tissue characteristic comprises a degree of edema, wherein edematous fluid has a relatively flat frequency response over a spectrum of frequencies provided by the pulses compared to a frequency response of living tissue.

6. The method as recited in claim 1, further comprising measuring the frequency response of the bodily tissue to the applied pulses at various times and trending a hemodynamic parameter based on the multiple frequency responses.

7. The method as recited in claim 6, wherein the hemodynamic parameter comprises one of: a congestive heart failure (CHF) index, a degree of pulmonary edema, a systolic slope, a cardiac contraction dZ/dt(max), a diastolic slope, a cardiac relaxation dZ/dt(min), a pre-ejection period, an ejection time, a left ventricular ejection fraction (LVEF), a diastolic heart failure index (DHFI), or a cardiac index.

8. A method, comprising:
generating pulses in an implantable device to apply to a bodily tissue via an electrode, wherein each pulse has a multi-phasic waveform having alternating positive and negative phases, wherein each phase comprises a duration and an amplitude, wherein duration is defined as the width of the phase and amplitude is defined as the length of the phase, wherein the alternating positive and negative phases have different absolute amplitudes, and wherein the multi-phasic waveform has a duration less than a charging time constant of an electrode-electrolyte interface between the electrode and the bodily tissue;
applying the pulses to the bodily tissue;
measuring a frequency response of the bodily tissue to the applied pulses; and
determining a tissue characteristic based on the frequency response.

9. The method as recited in claim 8, wherein the pulses possess a multi-phasic waveform that has alternating positive and negative phases that are charge-balanced and voltage-balanced.

10. The method as recited in claim 8, wherein determining the tissue characteristic comprises detecting a presence of infarcted tissue having a substantially flat frequency response over a spectrum of frequencies provided by the pulses.

11. The method as recited in claim 8, wherein determining the tissue characteristic comprises determining a blood-to-tissue ratio, wherein the blood has a substantially flat frequency response and the tissue has a capacitive frequency response over a spectrum of frequencies provided by the pulses.

12. The method as recited in claim 11, wherein the blood-to-tissue ratio is associated with an enlargement of a chamber of a patient's heart.

13. The method as recited in claim 8, wherein determining the tissue characteristic comprises detecting a degree of edema, wherein edematous fluid has a substantially flat frequency response over a spectrum of frequencies provided by the pulses compared to a frequency response of normal tissue.

14. The method as recited in claim 8, further comprising measuring the frequency response of the bodily tissue to the applied pulses at various times and trending a hemodynamic parameter based on the multiple frequency responses.

15. The method as recited in claim 14, wherein the hemodynamic parameter comprises one of: a congestive heart failure (CHF) index, a degree of pulmonary edema, a systolic slope, a cardiac contraction dZ/dt(max), a diastolic slope, a cardiac relaxation dZ/dt(min), a pre-ejection period, an ejection time, a left ventricular ejection fraction (LVEF), a diastolic heart failure index (DHFI), or a cardiac index.

16. A method, comprising:
generating pulses in an implantable device to apply to a bodily tissue via an electrode, wherein a multi-phasic waveform of each pulse possesses alternating positive and negative phases that have an additive net-zero charge and wherein the multi-phasic waveform is configured to generate a voltage on one or more capacitors of the bodily tissue and/or the implantable device in series with the impedance load of the bodily tissue path that has a zero-volt mean value, wherein each phase of the multi-phasic waveform comprises a duration and an amplitude, wherein duration is defined as the width of the phase and amplitude is defined as the length of the phase, wherein at least one negative phase has an absolute amplitude less than an absolute amplitude of one of the positive phases, and each pulse has a duration less than a charging time constant of an electrode-electrolyte interface between the electrode and the bodily tissue;
applying the pulses to the bodily tissue;
measuring a frequency response of the bodily tissue to the applied pulses; and
determining a tissue characteristic based on the frequency response.

17. The method as recited in claim 16, wherein the tissue characteristic comprises a presence of infarcted tissue having a substantially flat frequency response over a spectrum of frequencies provided by the pulses.

18. The method as recited in claim 16, wherein the tissue characteristic comprises a blood to tissue ratio, wherein the blood has a relatively flat frequency response and the tissue has a capacitive frequency response over a spectrum of frequencies provided by the pulses.

19. The method as recited in claim 18, wherein the blood to tissue ratio indicates enlargement of a chamber of a patient's heart.

20. The method as recited in claim 16, wherein the tissue characteristic comprises a degree of edema, wherein edematous fluid has a relatively flat frequency response over a spectrum of frequencies provided by the pulses compared to a frequency response of living tissue.

21. The method as recited in claim 16, further comprising measuring the frequency response of the bodily tissue to the applied pulses at various times and trending a hemodynamic parameter based on the multiple frequency responses.

22. The method as recited in claim 21, wherein the hemodynamic parameter comprises one of: a congestive heart failure (CHF) index, a degree of pulmonary edema, a systolic slope, a cardiac contraction dZ/dt(max), a diastolic slope, a cardiac relaxation dZ/dt(min), a pre-ejection period, an ejection time, a left ventricular ejection fraction (LVEF), a diastolic heart failure index (DHFI), or a cardiac index.

* * * * *